United States Patent
Damon et al.

(10) Patent No.: US 9,371,298 B2
(45) Date of Patent: Jun. 21, 2016

(54) PROCESSES FOR THE PREPARATION OF ISOTHIAZOLE DERIVATIVES

(71) Applicants: Pfizer Inc., New York, NY (US); OSI Pharmaceuticals, LLC, Northbrook, IL (US)

(72) Inventors: David B. Damon, Mystic, CT (US); Brian P. Jones, Waterford, CT (US)

(73) Assignees: Pfizer Inc., New York, NY (US); OSI Pharmaceuticals, LLC, Northbrook, IL (US)

(*) Notice: Subject to any disclaimer, the term of this patent is extended or adjusted under 35 U.S.C. 154(b) by 0 days.

(21) Appl. No.: 14/537,093

(22) Filed: Nov. 10, 2014

(65) Prior Publication Data

US 2015/0065726 A1   Mar. 5, 2015

Related U.S. Application Data

(62) Division of application No. 11/574,046, filed as application No. PCT/US2005/027398 on Aug. 2, 2005, now Pat. No. 8,884,025.

(60) Provisional application No. 60/604,542, filed on Aug. 26, 2004.

(51) Int. Cl.
C07D 275/03 (2006.01)

(52) U.S. Cl.
CPC .................... C07D 275/03 (2013.01)

(58) Field of Classification Search
USPC ........................................................ 548/213
See application file for complete search history.

(56) References Cited

U.S. PATENT DOCUMENTS

| | | | |
|---|---|---|---|
| 4,059,433 A | 11/1977 | Gibbons | |
| 6,235,764 B1 | 5/2001 | Larson et al. | |
| 6,380,214 B1 | 4/2002 | Gant et al. | |
| 6,548,526 B2 | 4/2003 | Larson et al. | |
| 2006/0035954 A1 | 2/2006 | Sharma et al. | |
| 2009/0023924 A1 | 1/2009 | Damon et al. | |

FOREIGN PATENT DOCUMENTS

| | | | |
|---|---|---|---|
| DE | 2408234 A1 | * | 9/1975 |
| GB | 2141711 A | * | 12/1984 |
| WO | 99/62890 A1 | | 12/1999 |
| WO | 2004/011461 A1 | | 2/2004 |

OTHER PUBLICATIONS

An English translation of Goerdeler et al., Chemische Berichte (1964), 97(11), pp. 3106-3117.*
An English translation of DE 2408234 A1, Sep. 4, 1975, Joos et al.*
Chan A.W.K. et al., "Isothiazole Chemistry-X Acylation, Alkylation and Tautomerism in 3-Hydroxyisothiazole", Tetrahedron 26:2497-2506 (1970).
Fleisher D. et al., "Improved Oral Drug Delivery: Solubility Limitations Overcome by the Use of Prodrugs", Advanced Drug Delivery Reviews 19:115-130 (1996).
Goerdeler J. et al., "Synthesis of 5-Amino-3-Hydroxy (-Alkoxy-, Amino-) Isothiazoles and of Derivatives of Pyrimidine-4-Thione", Chemische Berichte 97(11):3106-3117 (1964), together with an English-language abstract.
Goerdeler J. et al., CA 62:9101 (1965).
Johnson A.W., Invitation to Organic Chemistry, Sudbury, Massachusetts; Jones and Bartlett Publishers, pp. 531 and 546-550 (1999).
Robinson R.P. et al., "Discovery of the Hemifumarate and (α-L-Alanyloxy)Methyl Ether as Prodrugs of an Antirheumatic Oxindole: Prodrugs for the Enolic OH Group", Journal of Medicinal Chemistry 39(1):10-18 (1996).
Souillac et al., "Characterization of Delivery Systems", Differential Scanning Calorimetry Encyclopedia of Controlled Drug Delivery, John Wiley & Sons, pp. 212-227 (1999).
Vippagunta et al., "Crystalline Solids", Advanced Drug Delivery Reviews 48(1):3-26 (May 16, 2001).
International Search Report dated May 11, 2006 received from related Application No. PCT/US05/27398.
U.S. Office Action dated Jul. 15, 2010 issued in corresponding U.S. Appl. No. 11/574,046.
U.S. Final Office Action dated Jan. 6, 2011 issued in corresponding U.S. Appl. No. 11/574,046.
U.S. Office Action dated Apr. 26, 2013 issued in corresponding U.S. Appl. No. 11/574,046.
U.S. Final Office Action dated Oct. 9, 2013 issued in corresponding U.S. Appl. No. 11/574,046.

* cited by examiner

*Primary Examiner* — Laura L. Stockton
(74) *Attorney, Agent, or Firm* — Scully, Scott, Murphy & Presser, P.C.

(57) ABSTRACT

Processes and intermediates for the preparation of compounds of the Formula I

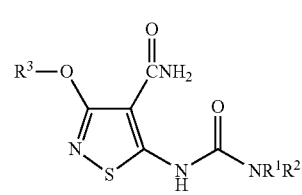

and the pharmaceutically acceptable salts, prodrugs, solvates and hydrates thereof, wherein $R^1$, $R^2$, and $R^3$ have the definitions provided herein.

2 Claims, No Drawings

PROCESSES FOR THE PREPARATION OF ISOTHIAZOLE DERIVATIVES

CROSS REFERENCE TO RELATED APPLICATIONS

This application is a divisional of U.S. application Ser. No. 11/574,046 filed on Feb. 21, 2007, which is a 371 filing of International Application No. PCT/US2005/027398 filed on Aug. 2, 2005 and claims the benefit of U.S. Provisional Application No. 60/604,542 dated Aug. 26, 2004.

BACKGROUND OF THE INVENTION

This invention relates to processes for preparing isothiazole derivatives that are useful in the treatment of hyperproliferative diseases, such as cancers, in mammals. It is known that polypeptide growth factors, such as vascular endothelial growth factor (VEGF), which has a high affinity for the human kinase insert-domain-containing receptor (KDR) or the murine fetal liver kinase 1 (FLK-1) receptor, have been associated with the proliferation of endothelial cells and more particularly to vasculogenesis and angiogenesis. The present invention provides a process for preparing compounds that are capable of binding to or modulating the KDR/FLK-1 receptor. The compounds may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

This invention also relates to processes for preparing intermediates that may be converted to the aforementioned isothiazole derivatives and to the intermediates prepared. Processes for preparing isothiazole derivatives and their intermediates have been disclosed in International Patent Publication WO 99/62890, published Dec. 9, 1999, and U.S. Pat. Nos. 6,235,764; 6,380,214; and 6,548,526, issuing on May 22, 2001, Apr. 30, 2002 and Apr. 15, 2003, respectively. Processes for preparing 3-alkoxyisothiazole derivatives as herbicides have been disclosed in U.S. Pat. No. 4,059,433, issuing on Nov. 22, 1977. Processes for preparing 5-amino-3-hydroxy(alkoxy,-amino-)isothiazoles have been disclosed in Chemische Berichte (1964), 97(11), 3106-17.

SUMMARY OF THE INVENTION

The present invention relates to a process for preparing a compound of the Formula I

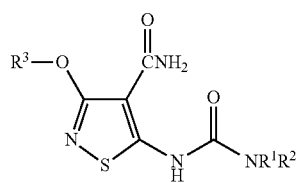

I or a pharmaceutically acceptable salt, prodrug, hydrate or solvate thereof; wherein $R^1$ is H, $C_1$-$C_{10}$ alkyl, $C_2$-$C_{10}$ alkenyl, $C_2$-$C_{10}$ alkynyl, —C(O)($C_1$-$C_{10}$ alkyl), —$(CH_2)_t$($C_6$-$C_{10}$ aryl), —$(CH_2)_t$(4-10 membered heterocyclic), —C(O)$(CH_2)_t$($C_6$-$C_{10}$ aryl), or —C(O)$(CH_2)_t$(4-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^1$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (═O) moiety; and the foregoing $R^1$ groups, except H, are optionally substituted by 1 to 3 $R^4$ groups;

$R^2$ is selected from the list of substituents provided in the definition of $R^1$, —$SO_2(CH_2)_t$($C_6$-$C_{10}$ aryl), —$SO_2(CH_2)_t$(4-10 membered heterocyclic), and —$OR^5$, t is an integer ranging from 0 to 5, and the foregoing $R^2$ groups are optionally substituted by 1 to 3 $R^4$ groups;

or $R^1$ and $R^2$ may be taken together with the nitrogen to which each is attached to form a 4-10 membered saturated monocyclic or polycyclic ring or a 5-10 membered heteroaryl ring, wherein said saturated and heteroaryl rings optionally include 1 or 2 heteroatoms selected from O, S and —N($R^6$)— in addition to the nitrogen to which $R^1$ and $R^2$ are attached, said —N($R^6$)— is optionally ═N— or —N═ where $R^1$ and $R^2$ are taken together as said heteroaryl group, said saturated ring optionally may be partially unsaturated by including 1 or 2 carbon-carbon double bonds, and said saturated and heteroaryl rings, including the $R^6$ group of said —N($R^6$)—, are optionally substituted by 1 to 3 $R^4$ groups;

$R^3$ is H, $C_1$-$C_{10}$ alkyl, $C_2$-$C_{10}$ alkenyl, $C_2$-$C_{10}$ alkynyl, —$(CH_2)_t$($C_6$-$C_{10}$ aryl), or —$(CH_2)_t$(4-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^3$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (═O) moiety; the —$(CH_2)_t$— moieties of the foregoing $R^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —C(O)$NR^5R^6$, —$NR^5R^6$, —$S(O)_jR^7$ wherein j is an integer ranging from 0 to 2, —$NR^5(CR^6R^7)_tOR^6$, —$(CH_2)_t$($C_6$-$C_{10}$ aryl), —$SO_2(CH_2)_t$($C_6$-$C_{10}$ aryl), —$S(CH_2)_t$($C_6$-$C_{10}$ aryl), —$O(CH_2)_t$($C_6$-$C_{10}$ aryl), —$(CH_2)_t$(4-10 membered heterocyclic), and —$(CR^6R^7)_mOR^6$, wherein m is an integer from 1 to 5 and t is an integer from 0 to 5; said alkyl group optionally contains 1 or 2 hetero moieties selected from O, S and —N($R^6$)— with the proviso that two O atoms, two S atoms, or an O and S atom are not attached directly to each other; said aryl and heterocyclic $R^4$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (═O) moiety; and the alkyl, aryl and heterocyclic moieties of the foregoing $R^4$ groups are optionally substituted by 1 to 3 substituents independently selected from nitro, trifluoromethyl, trifluoromethoxy, azido, —$NR^6SO_2R^5$, —$SO_2NR^5R^6$, —$NR^6C(O)R^5$, —C(O)$NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t$($C_6$-$C_{10}$ aryl), and —$(CH_2)_t$(4-10 membered heterocyclic), wherein t is an integer from 0 to 5; said alkyl group optionally includes 1 or 2 hetero moieties selected from O, S and —N(R⁶)— with the proviso that two O atoms, two S atoms, or an O and S atom are not attached directly to each other; said aryl and heterocyclic R⁵ groups are optionally fused to a $C_6$-$C_{10}$ aryl group, a $C_5$-$C_8$ saturated cyclic group, or a 4-10 membered heterocyclic group; and the foregoing R⁵ substituents, except H, are optionally substituted by 1 to 3 substituents independently selected from nitro, trifluoromethyl, trifluoromethoxy, azido, —NR⁶C(O)R⁷, —C(O)NR⁶R⁷, —NR⁶R⁷, hydroxy, $C_1$-$C_6$ alkyl, and $C_1$-$C_6$ alkoxy; and each R⁶ and R⁷ is independently H or $C_1$-$C_6$ alkyl; comprising reacting a compound of the Formula II

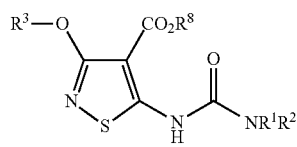

II wherein R⁸ is H, $C_1$-$C_{10}$ alkyl, —C(O)($C_1$-$C_{10}$ alkyl), —C(O)($C_6$-$C_{10}$ aryl), —C(O)(4-10 membered heterocyclic), —(CH₂)$_t$($C_6$-$C_{10}$ aryl), —(CH₂)$_t$(4-10 membered heterocyclic), —C(O)O($C_1$-$C_{10}$ alkyl); —C(O)O($C_6$-$C_{10}$ aryl), —C(O)O(4-10 membered heterocyclic) wherein t is an integer from 0 to 5; said aryl and heterocyclic R⁸ groups are optionally fused to a $C_6$-$C_{10}$ aryl group; and the foregoing aryl and heterocyclic R⁸ groups are optionally substituted with 1-2 substituents independently selected from halogen, trifluoromethyl, $C_1$-$C_6$ alkoxy, $C_1$-$C_6$ alkyl, and nitro groups; and R¹, R², R³, R⁴, R⁵, R⁶ and R⁷ are as defined above for the compound of the Formula I, with an ammonia source in a solvent to give a compound of the Formula I. The reaction is preferably performed at a temperature between about −50° C. and about 150° C. and pressures between about atmospheric pressure and about 200 psi, more preferably at a temperature of about 50° C. to about 700° C. at about 10 to about 40 psi, and still more preferably at about 30° C. to about 50° C. and at about 45 to about 80 psi. The ammonia source is preferably anhydrous ammonia, but the source of ammonia is not critical to the success of the invention. Other non-limiting sources of ammonia include ammonium hydroxide, liquid ammonia, ammonium chloride, sodamide, and formamide.

The reaction is preferably conducted in the presence of a solvent, such as $C_1$-$C_4$ alcohols (e.g., methanol, ethanol, propanol, 2-propanol), dipolar aprotic solvents (e.g., dimethyl sulfoxide, dimethylformamide, dimethylacetamide, 1-methyl-2-pyrrolidinone), ethers (e.g., tetrahydrofuran, diisopropyl ether, methyl-tert-butyl ether, dioxane, 2-methyltetrahydrofuran), water or mixtures of at least two thereof. Tetrahydrofuran and methanol or mixtures thereof are especially preferred.

An embodiment of the present invention refers to those processes and compounds where R² is H and R¹ is $C_1$-$C_{10}$ alkyl optionally substituted by 1 or 2 substituents independently selected from —NR⁵R⁶, —NR⁵(CR⁶R⁷)$_t$OR⁶ and —(CH₂)$_t$(4-10 membered heterocyclic) where t is an integer from 0 to 5. In another embodiment R¹ is selected from propyl, butyl, pentyl and hexyl, and may be optionally substituted with dimethylamino, hydroxy, pyrrolidinyl, morpholino, and ethyl-(2-hydroxy-ethyl)-amino, and R² is H.

In another embodiment R² is H and R¹ is —(CH₂)$_t$(4-10 membered heterocyclic) wherein t is an integer from 0 to 5, said heterocyclic group is optionally fused to a $C_6$-$C_{10}$ aryl group, a $C_5$-$C_8$ saturated cyclic group, or a 4-10 membered heterocyclic group and the R¹ group, including any fused portions of said R¹ group, may be substituted by 1 or 2 substituents independently selected from $C_1$-$C_4$ alkyl, hydroxy and hydroxymethyl.

In yet another embodiment R² is H and the 4-10 membered heterocyclic moiety of the R¹ group, when the t variable of the R¹ group ranges from 2-5, may be any one of morpholino, pyrrolidinyl, imidazolyl, piperazinyl, piperidinyl, and 2,5-diaza-bicyclo[2.2.1]hept-2-yl and the R¹ group is optionally substituted with hydroxy, hydroxymethyl and methyl.

An embodiment of the present invention refers to those processes and compounds wherein R³ is —(CH₂)$_t$($C_6$-$C_{10}$ aryl) wherein t is an integer from 1 to 3 and the R³ group is optionally substituted with 1 to 4 R⁴ groups. In another embodiment R³ is benzyl optionally substituted by 1 to 4 halo substituents.

In a preferred embodiment, the present invention refers to those processes and compounds wherein R² is H, R¹ is —(CH₂)₄-1-pyrrolidine, R³ is 2,6-difluoro-4-bromobenzyl, and R⁸ is methyl. Preferably, in this embodiment the compound of Formula II is reacted with anhydrous ammonia in methanol at 50° C. to 70° C. at 10 to 40 psi. Still more preferably, in this embodiment the compound of Formula II is reacted with anhydrous ammonia in methanol and tetrahydrofuran at 30° C. to 50° C. at 45 to 80 psi.

Another embodiment of the present invention refers to those processes wherein the compound of Formula I is selected from the group consisting of 3-(4-Bromo-2,6-difluoro-benzyloxy)-5-[3-(4-pyrrolidin-1-yl-butyl)-ureido}-isothiazole-4-carboxylic acid amide;
5-{3-[3-(4-Methyl-piperazin-1-yl)-propyl]-ureido}-3-(2,3,6-trifluoro-4-methyl-benzyloxy)-isothiazole-4-carboxylic acid amide;
3-(4-Chloro-2,6-difluoro-benzyloxy)-5-(3-{4-[ethyl-(2-hydroxy-ethyl)-amino]-butyl}-ureido)-isothiazole-4-carboxylic acid amide;
3-(2-Fluoro-4-methyl-benzyloxy)-5-{3-[3-(4-methyl-piperazin-1-yl)-propyl]-ureido}-isothiazole-4-carboxylic acid amide;
3-(2,5-Difluoro-4-methyl-benzyloxy)-5-(3-4-[4-(2-hydroxy-ethyl)-piperazin-1-yl]-butyl}-ureido)-isothiazole-4-carboxylic acid amide;
3-(2,5-Difluoro-4-methyl-benzyloxy)-5-[3-(6-dimethylamino-hexyl)-ureido]-isothiazole-4-carboxylic acid amide;
3-(2-Fluoro-4-methyl-benzyloxy)-5-[3-(5-isopropylaminopentyl)-ureido]-isothiazole-4-carboxylic acid amide;
hydrochloride salt of 3-(4-Bromo-2,6-difluoro-benzyloxy)-5-[3-(4-pyrrolidin-1-yl-butyl)-ureido}-isothiazole-4-carboxylic acid amide;
3-(4-Chloro-2,6-difluoro-benzyloxy)-5-[3-(4-pyrrolidin-1-yl-butyl)-ureido]-isothiazole-4-carboxylic acid amide;
3-(4-Chloro-2,6-difluoro-benzyloxy)-5-{3-[3-(4-methyl-piperazin-1-yl)-propyl]-ureido}-isothiazole-4-carboxylic acid amide;
3-(4-Chloro-2,6-difluoro-benzyloxy)-5-{3-[-(1-methyl-pyrrolidin-2-yl)-ethyl]-ureido}-isothiazole-4-carboxylic acid amide;
3-(2,6-Difluoro-4-methyl-benzyloxy)-5-[3-(4-pyrrolidin-1-yl-butyl)-ureido]-isothiazole-4-carboxylic acid amide;
3-(2,6-Difluoro-4-methyl-benzyloxy)-5-[3-{4-[4-(2-hydroxy-ethyl)-piperazin-1-yl]-butyl}-ureido)-isothiazole-4-carboxylic acid amide;
3-(4-Chloro-2,6-difluoro-benzyloxy)-5-[3-(3-hydroxy-5-pyrrolidin-1-yl)-pentyl)-ureido]-isothiazole-4-carboxylic acid amide;

3-(2,5-Difluoro-4-methyl-benzyloxy)-5-{3-[4-(3,4-dihydroxy-pyrrolidin-1-yl]-butyl]-ureido}-isothiazole-4-carboxylic acid amide;
3-(4-Chloro-2,6-difluoro-benzyloxy)-5-{3-[4-(3,4-dihydroxy-pyrrolidin-1-yl)-butyl]-ureido}-isothiazole-4-carboxylic acid amide;
3-(2,5-Difluoro-4-methyl-benzyloxy)-5-{3-[4-(2-hydroxymethyl-pyrrolidin-1-yl)-butyl]-ureido}-isothiazole-4-carboxylic acid amide;
3-(4-Chloro-2,6-difluoro-benzyloxy)-5-{3-[4-(2-hydroxymethyl-pyrrolidin-1-yl)-butyl]-ureido}-isothiazole-4-carboxylic acid amide;
3-(2,5-Difluoro-4-methyl-benzyloxy)-5-{3-[4-(3-hydroxy-pyrrolidin-1-yl)-butyl]-ureido}-isothiazole-4-carboxylic acid amide;
3-(4-Bromo-2,6-difluoro-benzyloxy)-5-[3-(4-pyrrolidin-1-yl-butyl)-ureido}-isothiazole-4-carboxylic acid amide;
3-(2,6-Difluoro-4-methyl-benzyloxy)-5-[3-(4-hydroxy-5-piperidin-1-yl-pentyl)-ureido]-isothiazole-4-carboxylic acid amide;
3-(2,5-Difluoro-4-methyl-benzyloxy)-5-{3-[4-(3-hydroxy-5-piperidin-1-yl-pentyl)-ureido]-isothiazole-4-carboxylic acid amide;
3-(4-Chloro-2,6-difluoro-benzyloxy)-5-{3-[4-(2-hydroxymethyl-piperidin-1-yl)-butyl]-ureido}-isothiazole-4-carboxylic acid amide;
3-(2,5-Difluoro-4-methyl-benzyloxy)-5-(3-{4-[ethyl-(2-hydroxy-ethyl)-amino]-butyl}-ureido)-isothiazole-4-carboxylic acid amide;
3-(4-Chloro-2,6-difluoro-benzyloxy)-5-[3-(5-hydroxy-6-piperidin-1-yl)-hexyl)-ureido}-isothiazole-4-carboxylic acid amide;
3-(4-Bromo-2,3,6-trifluoro-benzyloxy)-5-{3-[3-(4-methyl-piperazin-1-yl)-propyl]-ureido}-isothiazole-4-carboxylic acid amide;
3-(2,6-Difluoro-4-methyl-benzyloxy)-5-{3-[3-(4-methyl-piperazin-1-yl)-propyl]-ureido}-isothiazole-4-carboxylic acid amide;
3-(2,6-Difluoro-4-methyl-benzyloxy)-5-[3-(3-hydroxy-5-pyrrolidin-1-yl-pentyl)-ureido]-isothiazole-4-carboxylic acid amide;
5-[3-(4-Pyrrolidin-1-yl-butyl)-ureido]-3-(2,3,6-trifluoro-4-methyl-benzyloxy)-isothiazole-4-carboxylic acid amide;
5-[3-(3-Hydroxy-5-pyrrolidin-1-yl-pentyl)-ureido]-3-(2,3,6-trifluoro-4-methyl-benzyloxy)-isothiazole-4-carboxylic acid amide;
3-(4-Chloro-2,6-difluoro-benzyloxy)-5-{3-[3-(5-methyl-2,5-diazabicyclo[2.2.1]hept-2-yl)-propyl]-ureido}-isothiazole-4-carboxylic acid amide;
3-(4-Chloro-2,3,6-trifluoro-benzyloxy)-5-{3-[3-(5-methyl-2,5-diaza-bicyclo[2.2.1]hept-2-yl)-propyl]-ureido}-isothiazole-4-carboxylic acid amide;
3-(4-Chloro-2,3,6-trifluoro-benzyloxy)-5-(3-[2-(1-methyl-pyrrolidin-2-yl)-ethyl]-ureido}-isothiazole-4-carboxylic acid amide;
3-(4-Chloro-2,3,6-trifluoro-benzyloxy)-5-[3-(4-pyrrolidin-1-yl-butyl)-ureido]-isothiazole-4-carboxylic acid amide;
3-(4-Chloro-2,3,6-trifluoro-benzyloxy)-5-{3-[4-(2-hydroxymethyl-pyrrolidin-1-yl)-butyl]-ureido}-isothiazole-4-carboxylic acid amide;
5-{3-[2-(1-Methyl-pyrrolidin-2-yl)-ethyl]-ureido}-3-(2,3,6-trifluoro-4-methyl-benzyloxy)-isothiazole-4-carboxylic acid amide;
5-[3-(4-Dimethylamino-butyl)-ureido]-3-(2,3,6-trifluoro-4-methyl-benzyloxy)-isothiazole-4-carboxylic acid amide;
5-[3-(3-Dimethylamino-propyl)-ureido]-3-(2,3,6-trifluoro-4-methyl-benzyloxy)-isothiazole-4-carboxylic acid amide;
5-[3-(3-Hydroxy-5-isopropylamino-pentyl)-ureido]-3-(2,3,6-trifluoro-4-methyl-benzyloxy)-isothiazole-4-carboxylic acid amide;
5-[3-(3-Isopropylamino-propyl)-ureido]-3-(2,3,6-trifluoro-4-methyl-benzyloxy)-isothiazole-4-carboxylic acid amide;
5-{3-[4-(4-Methyl-piperazin-1-yl)-butyl]-ureido}-3-(2,3,6-trifluoro-4-methyl-benzyloxy)-isothiazole-4-carboxylic acid amide;
5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid amide;
5-[3-(3-Pyrrolidin-1-yl-propyl)-ureido]-3-(2,3,6-trifluoro-4-methyl-benzyloxy)-isothiazole-4-carboxylic acid amide;
5-[3-(4-Hydroxy-5-piperidin-1-yl-pentyl)-ureido]-3-(2,3,6-trifluoro-4-methyl-benzyloxy)-isothiazole-4-carboxylic acid amide;
3-(4-Chloro-2,6-difluoro-benzyloxy)-5-[3-(4-imidazol-1-yl-butyl)-ureido]-isothiazole-4-carboxylic acid amide;
5-(3-{4-[Ethyl-(2-hydroxy-ethyl)-amino]-butyl}-ureido)-3-(2,3,6-trifluoro-4-methyl-benzyloxy)-isothiazole-4-carboxylic acid amide;
3-(4-Chloro-(2,3,6-trifluoro-benzyloxy)-5-{3-[4-(2-hydroxmethyl-piperidin-1-yl)-butyl]-ureido}-isothiazole-4-carboxylic acid amide;
3-(4-Chloro-2,3,6-trifluoro-benzyloxy)-5-[3-(3-hydroxy-5-pyrrolidin-1-yl-pentyl)-ureido]-isothiazole-4-carboxylic acid amide;
3-(4-Bromo-2,6-difluoro-benzyloxy)-5-{3-[3-(4-methyl-piperazin-1-yl)-propyl]-ureido}-isothiazole-4-carboxylic acid amide;
3-(2,6-Difluoro-4-methyl-benzyloxy)-5-{3-[2-(1-methyl-pyrrolidin-2-yl)-ethyl]-ureido}-isothiazole-4-carboxylic acid amide;
3-(2,6-Difluoro-4-methyl-benzyloxy)-5-[3-(4-dimethylamino-butyl)-ureido}-isothiazole-4-carboxylic acid amide;
3-(2,6-Difluoro-4-methyl-benzyloxy)-5-[3-(3-dimethylamino-propyl)-ureido]-isothiazole-4-carboxylic acid amide;
3-(4-Bromo-2,3,6-trifluoro-benzyloxy)-5-[3-(4-pyrrolidin-1-yl-butyl)-ureido]-isothiazole-4-carboxylic acid amide;
3-(4-Chloro-2,3,6-trifluoro-benzyloxy)-5-[3-(4-imidazol-1-yl-butyl)-ureido]-isothiazole-4-carboxylic acid amide;
3-(4-Chloro-2,3,6-difluoro-benzyloxy)-5-(3-{3-[ethyl-(2-hydroxy-ethyl)-amino]-propyl}-ureido)-isothiazole-4-carboxylic acid amide;
3-(4-Chloro-2,3,6-trifluoro-benzyloxy)-5-(3-{3-[ethyl-(2-hydroxy-ethyl)-amino]-propyl}-ureido)-isothiazole-4-carboxylic acid amide;
5-[3-(3-Methylamino-propyl)-ureido]-3-(2,3,6-trifluoro-4-methyl-benzyloxy)-isothiazole-4-carboxylic acid amide;
5-[3-(3-Amino-propyl)-3-methyl-ureido]-3-(2,3,6-trifluoro-4-methyl-benzyloxy)-isothiazole-4-carboxylic acid amide;
5-[3-(4-Diethylamino-butyl)-ureido]-3-(2,3,6-trifluoro-4-methyl-benzyloxy)-isothiazole-4-carboxylic acid amide;
3-(2,6-Difluoro-4-methyl-benzyloxy)-5-[3-(3-pyrrolidin-1-yl-propyl)-ureido]-isothiazole-4-carboxylic acid amide;
3-(3-Chloro-2,6-difluoro-4-methyl-benzyloxy)-5-[3-(4-dimethylamino-butyl)-ureido]-isothiazole-4-carboxylic acid amide;

5-(3-{4-[Bis-(2-hydroxy-ethyl)-amino]-butyl}-ureido)-3-(2,6-difluoro-4-methyl-benzyloxy)-isothiazole-4-carboxylic acid amide;

and the pharmaceutically acceptable salts, prodrugs, hydrates and solvates of said compounds.

In an especially preferred embodiment, the present invention refers to those processes wherein the compound of Formula I is 3-(4-Bromo-2,6-difluoro-benzyloxy)-5-[3-(4-pyrrolidin-1-yl-butyl]-ureido}-isothiazole-4-carboxylic acid amide and the pharmaceutically acceptable salts, prodrugs, hydrates and solvates thereof.

The present invention also relates to a process for the preparation of a compound of the Formula II

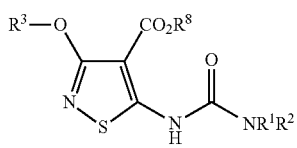

or a pharmaceutically acceptable salt thereof; wherein $R^1$, $R^2$, $R^3$, $R^4$, $R^5$, $R^6$, $R^7$, and $R^8$ are as defined above for Formula I; comprising (1) reacting a compound of Formula IV

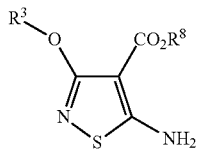

wherein $R^3$, $R^4$, $R^5$, $R^6$, $R^7$ and $R^8$ are as defined above for Formula II with a source of carbonyl, with or without an added base, and then adding a compound of Formula III

HNR$^1$R$^2$      III wherein $R^1$ and $R^2$ are as defined above for Formula II, in a solvent to give a compound of the Formula II or (2) reacting a compound of Formula III with a source of carbonyl, with or without an added base; and then adding a compound of Formula IV in a solvent to give a compound of the Formula II.

The source of carbonyl may be any suitable carbonyl source known to those skilled in the art. In one embodiment the source of carbonyl is represented by the Formula

R'OCOX' wherein R' is a $C_1$-$C_4$ alkyl or $C_6$-$C_{10}$ aryl, and X' is a leaving group such as a chloro group. Alternatively, other non-limiting examples of suitable carbonyl sources include 1,1'-carbonyldiimidazole, di-tert-butyl-dicarbonate in the presence of 4-dimethylaminopyridine and phosgene or its equivalents such as diphosgene or triphosgene.

The reaction may be carried out at a temperature of between about −78° C. to about 100° C., and preferably between about 15° C. and about 25° C.

The reaction may utilize any suitable base known to those skilled in the art. Non-limiting examples of a suitable base include tertiary amines (e.g. triethylamine, diisopropylethylamine, pyridine, 4-dimethylaminopyridine), alkali metal carbonates, and alkali metal hydrogen carbonates.

The reaction may occur in any suitable solvent known to those skilled in the art. Preferably, the reaction is carried out in the presence of a halogenated hydrocarbon solvent such as dichloromethane or chloroform; an ether such as tetrahydrofuran, diisopropyl ether, methyl-tert-butyl ether, and 2-methyltetrahydrofuran; a dipolar aprotic solvent such as dimethylsulfoxide, dimethylformamide, 1-methyl-2-pyrrolidinone, and dimethylacetamide, and mixtures thereof.

In a preferred embodiment the compound of Formula IV is treated with triphosgene and triethylamine in dichloromethane at a temperature of between about −78° C. to about 20° C., then a compound of Formula III is added, preferably a compound of Formula III wherein $R^1$ is H and $R^2$ is —(CH$_2$)$_4$-1-pyrrolidino, to give a compound of Formula II.

In a more preferred embodiment, the present invention refers to those processes wherein the compound of Formula II is 3-(4-Bromo-2,6-difluoro-benzyloxy)-5-[3-(4-pyrrolidin-1-yl-butyl)-ureido]-isothiazole-4-carboxylic acid methyl ester.

In a more preferred embodiment the compound of Formula III wherein $R^1$ is H and $R^2$ is —(CH$_2$)$_4$-1-pyrrolidine is treated with 1,1'-carbonyldiimidazole in tetrahydrofuran at a temperature of about −10° C. to about 10° C. to produce a product that is added to a compound of Formula IV in dimethylsulfoxide and potassium carbonate at a temperature of about 15° C. to about 25° C., to give a compound of the Formula II, which is preferably 3-(4-Bromo-2,6-difluoro-benzyloxy)-5-[3-(4-pyrrolidin-1-yl-butyl)-ureido]-isothiazole-4-carboxylic acid methyl ester.

Another embodiment of the present invention refers to those processes wherein the compound of Formula II is selected from the group consisting of 3-(4-Bromo-2,6-difluoro-benzyloxy)-5-[3-(4-pyrrolidin-1-yl-butyl)-ureido}-isothiazole-4-carboxylic acid methyl ester;

5-{3-[3-(4-Methyl-piperazin-1-yl)-propyl]-ureido}-3-(2,3,6-trifluoro-4-methyl-benzyloxy)-isothiazole-4-carboxylic acid methyl ester;

3-(4-Chloro-2,6-difluoro-benzyloxy)-5-(3-{4-[ethyl-(2-hydroxy-ethyl)-amino]-butyl}-ureido)-isothiazole-4-carboxylic acid methyl ester;

3-(2-Fluoro-4-methyl-benzyloxy)-5-{3-[3-(4-methyl-piperazin-1-yl)-propyl]-ureido}-isothiazole-4-carboxylic acid methyl ester;

3-(2,5-Difluoro-4-methyl-benzyloxy)-5-(3-4-[4-(2-hydroxy-ethyl)-piperazin-1-yl]-butyl}-ureido)-isothiazole-4-carboxylic acid methyl ester;

3-(2,5-Difluoro-4-methyl-benzyloxy)-5-[3-(6-dimethylamino-hexyl)-ureido]-isothiazole-4-carboxylic acid methyl ester;

3-(2-Fluoro-4-methyl-benzyloxy)-5-[3-(5-isopropylamino-pentyl)-ureido]-isothiazole-4-carboxylic acid methyl ester;

hydrochloride salt of 3-(4-Bromo-2,6-difluoro-benzyloxy)-5-[3-(4-pyrrolidin-1-yl-butyl)-ureido}-isothiazole-4-carboxylic acid methyl ester;

3-(4-Chloro-2,6-difluoro-benzyloxy)-5-[3-(4-pyrrolidin-1-yl-butyl)-ureido]-isothiazole-4-carboxylic acid methyl ester;

3-(4-Chloro-2,6-difluoro-benzyloxy)-5-{3-[3-(4-methyl-piperazin-1-yl)-propyl]-ureido}-isothiazole-4-carboxylic acid methyl ester;

3-(4-Chloro-2,6-difluoro-benzyloxy)-5-{3-[-(1-methyl-pyrrolidin-2-yl)-ethyl]-ureido}-isothiazole-4-carboxylic acid methyl ester;

3-(2,6-Difluoro-4-methyl-benzyloxy)-5-[3-(4-pyrrolidin-1-yl-butyl)-ureido]-isothiazole-4-carboxylic acid methyl ester;

3-(2,6-Difluoro-4-methyl-benzyloxy)-5-[3-{4-[4-(2-hydroxy-ethyl)-piperazin-1-yl]-butyl}-ureido)-isothiazole-4-carboxylic acid methyl ester;

3-(4-Chloro-2,6-difluoro-benzyloxy)-5-[3-(3-hydroxy-5-pyrrolidin-1-yl)-pentyl)-ureido}-isothiazole-4-carboxylic acid methyl ester;

3-(2,5-Difluoro-4-methyl-benzyloxy)-5-[3-[4-(3,4-dihydroxy-pyrrolidin-1-yl]-butyl]-ureido}-isothiazole-4-carboxylic acid methyl ester;

3-(4-Chloro-2,6-difluoro-benzyloxy)-5-{3-[4-(3,4-dihydroxy-pyrrolidin-1-yl]-butyl]-ureido}-isothiazole-4-carboxylic acid methyl ester;

3-(2,5-Difluoro-4-methyl-benzyloxy)-5-{3-[4-(2-hydroxymethyl-pyrrolidin-1-yl)-butyl]-ureido}-isothiazole-4-carboxylic acid methyl ester;

3-(4-Chloro-2,6-difluoro-benzyloxy)-5-{3-[4-(2-hydroxyethyl-pyrrolidin-1-yl)-butyl]-ureido}-isothiazole-4-carboxylic acid methyl ester;

3-(2,5-Difluoro-4-methyl-benzyloxy)-5-{3-[4-(3-hydroxy-pyrrolidin-1-yl)-butyl]-ureido}-isothiazole-4-carboxylic acid methyl ester;

3-(4-Bromo-2,6-difluoro-benzyloxy)-5-[3-(4-pyrrolidin-1-yl-butyl]-ureido}-isothiazole-4-carboxylic acid methyl ester;

3-(2,6-Difluoro-4-methyl-benzyloxy)-5-[3-(4-hydroxy-5-piperidin-1-yl-pentyl)-ureido]-isothiazole-4-carboxylic acid methyl ester;

3-(2,5-Difluoro-4-methyl-benzyloxy)-5-{3-[4-(3-hydroxy-5-piperidin-1-yl-pentyl)-ureido]-isothiazole-4-carboxylic acid methyl ester;

3-(4-Chloro-2,6-difluoro-benzyloxy)-5-{3-[4-(2-hydroxyethyl-piperidin-1-yl)-butyl]-ureido}-isothiazole-4-carboxylic acid methyl ester;

3-(2,5-Difluoro-4-methyl-benzyloxy)-5-(3-{4-[ethyl-(2-hydroxy-ethyl)-amino]-butyl}-ureido)-isothiazole-4-carboxylic acid methyl ester;

3-(4-Chloro-2,6-difluoro-benzyloxy)-5-[3-(5-hydroxy-6-piperidin-1-yl)-hexyl)-ureido}-isothiazole-4-carboxylic acid methyl ester;

3-(4-Bromo-2,3,6-trifluoro-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-[3-(3-hydroxy-5-pyrrolidin-1-yl-pentyl)-ureido]-isothiazole-4-carboxylic acid methyl ester;

5-[3-(4-Pyrrolidin-1-yl-butyl)-ureido]-3-(2,3,6-trifluoro-4-methyl-benzyloxy)-isothiazole-4-carboxylic acid methyl ester;

5-[3-(3-Hydroxy-5-pyrrolidin-1-yl-pentyl)-ureido]-3-(2,3,6-trifluoro-4-methyl-benzyloxy)-isothiazole-4-carboxylic acid methyl ester;

3-(4-Chloro-2,6-difluoro-benzyloxy)-5-{3-[3-(5-methyl-2,5-diazabicyclo[2.2.1]hept-2-yl)-propyl]-ureido}-isothiazole-4-carboxylic acid methyl ester;

3-(4-Chloro-2,3,6-trifluoro-benzyloxy)-5-{3-[3-(5-methyl-2,5-diaza-bicyclo[2.2.1]hept-2-yl)-propyl]-ureido}-isothiazole-4-carboxylic acid methyl ester;

3-(4-Chloro-2,3,6-trifluoro-benzyloxy)-5-{3-[2-(1-methyl-pyrrolidin-2-yl)-ethyl]-ureido}-isothiazole-4-carboxylic acid methyl ester;

3-(4-Chloro-2,3,6-trifluoro-benzyloxy)-5-[3-(4-pyrrolidin-1-yl-butyl)-ureido]-isothiazole-4-carboxylic acid methyl ester;

3-(4-Chloro-2,3,6-trifluoro-benzyloxy)-5-{3-[4-(2-hydroxymethyl-pyrrolidin-1-yl)-butyl]-ureido}-isothiazole-4-carboxylic acid methyl ester;

5-{3-[2-(1-Methyl-pyrrolidin-2-yl)-ethyl]-ureido}-3-(2,3,6-trifluoro-4-methyl-benzyloxy)-isothiazole-4-carboxylic acid methyl ester;

5-[3-(4-Dimethylamino-butyl)-ureido]-3-(2,3,6-trifluoro-4-methyl-benzyloxy)-isothiazole-4-carboxylic acid methyl ester;

5-[3-(3-Dimethylamino-propyl)-ureido]-3-(2,3,6-trifluoro-4-methyl-benzyloxy)-isothiazole-4-carboxylic acid methyl ester;

5-[3-(3-Hydroxy-5-isopropylamino-pentyl)-ureido]-3-(2,3,6-trifluoro-4-methyl-benzyloxy)-isothiazole-4-carboxylic acid methyl ester;

5-[3-(3-isopropylamino-propyl)-ureido]-3-(2,3,6-trifluoro-4-methyl-benzyloxy)-isothiazole-4-carboxylic acid methyl ester;

5-{3-[4-(4-Methyl-piperazin-1-yl)-butyl]-ureido}-3-(2,3,6-trifluoro-4-methyl-benzyloxy)-isothiazole-4-carboxylic acid methyl ester;

5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid methyl ester;

5-[3-(3-Pyrrolidin-1-yl-propyl)-ureido]-3-(2,3,6-trifluoro-4-methyl-benzyloxy)-isothiazole-4-carboxylic acid methyl ester;

5-[3-(4-Hydroxy-5-piperidin-1-yl-pentyl)-ureido]-3-(2,3,6-trifluoro-4-methyl-benzyloxy)-isothiazole-4-carboxylic acid methyl ester;

3-(4-Chloro-2,6-difluoro-benzyloxy)-5-[3-(4-imidazol-1-yl-butyl)-ureido]-isothiazole-4-carboxylic acid methyl ester;

5-(3-{4-[Ethyl-(2-hydroxy-ethyl)-amino]-butyl}-ureido)-3-(2,3,6-trifluoro-4-methyl-benzyloxy)-isothiazole-4-carboxylic acid methyl ester;

3-(4-Chloro-(2,3,6-trifluoro-benzyloxy)-5-{3-[4-(2-hydroxmethyl-piperidin-1-yl)-butyl]-ureido}-isothiazole-4-carboxylic acid methyl ester;

3-(4-Chloro-2,3,6-trifluoro-benzyloxy)-5-[3-(3-hydroxy-5-pyrrolidin-1-yl-pentyl)-ureido]-isothiazole-4-carboxylic acid methyl ester;

3-(4-Bromo-2,6-difluoro-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-{3-[2-(1-methyl-pyrrolidin-2-yl)-ethyl]-ureido}-isothiazole-4-carboxylic acid methyl ester;

3-(2,6-Difluoro-4-methyl-benzyloxy)-5-[3-(4-dimethylamino-butyl)-ureido]-isothiazole-4-carboxylic acid methyl ester;

3-(2,6-Difluoro-4-methyl-benzyloxy)-5-[3-(3-dimethylamino-propyl)-ureido]-isothiazole-4-carboxylic acid methyl ester;

3-(4-Bromo-2,3,6-trifluoro-benzyloxy)-5-[3-(4-pyrrolidin-1-yl-butyl)-ureido]-isothiazole-4-carboxylic acid methyl ester;

3-(4-Chloro-2,3,6-trifluoro-benzyloxy)-5-[3-(4-imidazol-1-yl-butyl)-ureido]-isothiazole-4-carboxylic acid methyl ester;

3-(4-Chloro-2,3,6-difluoro-benzyloxy)-5-(3-{3-[ethyl-(2-hydroxy-ethyl)-amino]-propyl}-ureido)-isothiazole-4-carboxylic acid methyl ester;

3-(4-Chloro-2,3,6-trifluoro-benzyloxy)-5-(3-{3-[ethyl-(2-hydroxy-ethyl)-amino]-propyl}-ureido)-isothiazole-4-carboxylic acid methyl ester;

5-[3-(3-Methylamino-propyl)-ureido]-3-(2,3,6-trifluoro-4-methyl-benzyloxy)-isothiazole-4-carboxylic acid methyl ester;

5-[3-(3-Amino-propyl)-3-methyl-ureido]-3-(2,3,6-trifluoro-4-methyl-benzyloxy)-isothiazole-4-carboxylic acid methyl ester;

5-[3-(4-Diethylamino-butyl)-ureido]-3-(2,3,6-trifluoro-4-methyl-benzyloxy)-isothiazole-4-carboxylic acid methyl ester;

3-(2,6-Difluoro-4-methyl-benzyloxy)-5-[3-(3-pyrrolidin-1-yl-propyl)-ureido]-isothiazole-4-carboxylic acid methyl ester;

3-(3-Chloro-2,6-difluoro-4-methyl-benzyloxy)-5-[3-(4-dimethylamino-butyl)-ureido]-isothiazole-4-carboxylic acid methyl ester;

5-(3-{4-[Bis-(2-hydroxy-ethyl)-amino]-butyl}-ureido)-3-(2,6-difluoro-4-methyl-benzyloxy)-isothiazole-4-carboxylic acid methyl ester;

and pharmaceutically acceptable salts thereof.

The present invention also relates to a process for the preparation of a compound of Formula IV

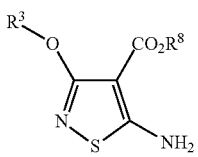

IV or a pharmaceutically acceptable salt thereof; wherein $R^3$, $R^4$, $R^5$, $R^6$, $R^7$, and $R^8$ are as defined above;
comprising reacting a compound of the Formula V

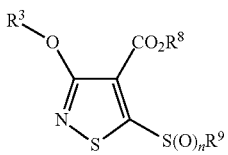

V wherein
$R^3$, $R^4$, $R^5$, $R^6$, $R^7$ and $R^8$ are as defined above; $R^9$ is $C_1$-$C_{10}$ alkyl, $C_6$-$C_{10}$ aryl, 4-10 membered heterocyclic, said aryl and heterocyclic $R^9$ groups are optionally fused to a $C_6$-$C_{10}$ aryl group; and the foregoing aryl and heterocyclic $R^9$ groups are optionally substituted independently with 1-2 substituents independently selected from halogen, trifluoromethyl, $C_1$-$C_6$ alkoxy, $C_1$-$C_6$ alkyl, and nitro groups; and
n is 0, 1, or 2;
with an ammonia source in a solvent to give a compound of the Formula IV. The reaction is preferably performed at a temperature between about −50° C. to about 150° C. and pressures between about atmospheric pressure and about 200 psi, more preferably at a temperature of about 20° C. to about 60° C. at about atmospheric pressure to about 50 psi, and still more preferably at a temperature of about 40° C. to about 50° C. and at about 45-55 psi. The ammonia source is preferably anhydrous ammonia, but the source of ammonia is not critical to the success of the invention. Other non-limiting sources of ammonia include ammonium hydroxide and liquid ammonia.

The reaction is preferably conducted in the presence of a solvent, such as water, $C_1$-$C_4$ alcohols (e.g., methanol, ethanol, propanol, isopropanol), ethers (e.g., tetrahydrofuran, diisopropyl ether, methyl-tert-butyl ether, dioxane, 2-methyltetrahydrofuran), and dipolar aprotic solvents (e.g., dimethylsulfoxide, dimethylformamide, 1-methyl-2-pyrrolidinone, and dimethylacetamide).

An embodiment of the present invention refers to those processes wherein the compound of Formula V is reacted with an ammonia source in a solvent to give a compound of Formula IV and wherein $R^3$ is —$(CH_2)_t$($C_6$-$C_{10}$ aryl) wherein t is an integer from 1 to 3 and the $R^3$ group is optionally substituted with 1 to 4 $R^4$ groups. In another embodiment $R^3$ is benzyl optionally substituted by 1 to 4 halo substituents.

In a preferred embodiment, the present invention refers to those processes wherein the compound of Formula V is reacted with an ammonia source in a solvent to give a compound of Formula IV wherein $R^3$ is 2,6-difluoro-4-bromobenzyl, $R^8$ is methyl, $R^9$ is methyl; and n is 2. Preferably in this embodiment the compound of Formula V is reacted with anhydrous ammonia in methanol or dimethylsulfoxide at 20° C. to 60° C. at atmospheric pressure to 50 psi. Still more preferably, in this embodiment the compound of Formula V is reacted with anhydrous ammonia in tetrahydrofuran, and preferably at about 40° C. to about 50° C. at 45 to 55 psi.

In an especially preferred embodiment, the present invention refers to those processes wherein the compound of Formula IV is 5-Amino-3-(4-bromo-2,6-difluoro-benzyloxy)-isothiazole-4-carboxylic acid methyl ester.

The present invention also relates to a process for the preparation of a compound of Formula V

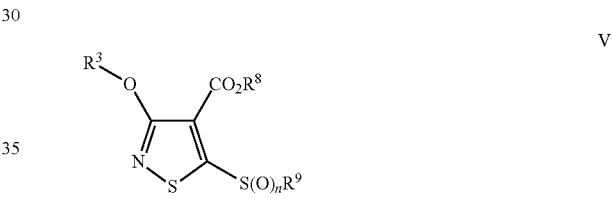

V or a pharmaceutically acceptable salt thereof; wherein
$R^3$, $R^4$, $R^5$, $R^6$, $R^7$, $R^8$, and $R^9$ are as defined above; and
n is 0, 1, or 2;
comprising reacting a compound of the Formula VII

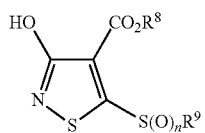

VII wherein n, $R^8$, and $R^9$ are as defined above, with a compound of Formula VI $R^3X$      VI wherein $R^3$ is as defined above and X is a halogen such as chlorine, bromine or iodine; hydroxyl; $C_1$-$C_4$ alkyl sulfonate ester; aryl sulfonate ester such as tosylate, nosylate, besylate or brosylate; or an imidate such as trichloromethyl imidate in the presence of an acid, a base, or Mitsunobu reagents R'$_3$P and R"OC(O)N=NC(O)OR" wherein each R' and R" is independently $C_1$-$C_4$ alkyl or $C_6$-$C_{10}$ aryl, and wherein said R' and R" alkyl and aryl groups are optionally substituted with 1 to 3 $R^{10}$ groups;

$R^{10}$ is $C_1$-$C_{10}$ alkyl, $C_2$-$C_{10}$ alkenyl, $C_2$-$C_{10}$ alkynyl, nitro, trifluoromethyl, trifluoromethoxy, —$OR^5$, —$NR^6C(O)OR^5$, —$NR^6SO_2R^5$, —$SO_2NR^5R^6$, —$NR^6C(O)R^5$, —C(O)

NR$^5$R$^6$, —NR$^5$R$^6$, —S(O)$_j$R$^7$ wherein j is an integer ranging from 0 to 2, —NR$^5$(CR$^6$R$^7$)$_t$OR$^6$, —(CH$_2$)$_t$(C$_6$-C$_{10}$ aryl), —SO$_2$(CH$_2$)$_t$(C$_6$-C$_{10}$ aryl), —S(CH$_2$)$_t$(C$_6$-C$_{10}$ aryl), —O(CH$_2$)$_t$(C$_6$-C$_{10}$ aryl), —(CH$_2$)$_t$(4-10 membered heterocyclic), and —(CR$^6$R$^7$)$_m$OR$^6$, wherein m is an integer from 1 to 5 and t is an integer from 0 to 5; said C$_1$-C$_{10}$ alkyl group optionally contains 1 or 2 hetero moieties selected from O, S and —N(R$^6$)— with the proviso that two O atoms, two S atoms, or an O and S atom are not attached directly to each other; said —(CH$_2$)$_t$(C$_6$-C$_{10}$ aryl), —SO$_2$(CH$_2$)$_t$(C$_6$-C$_{10}$ aryl), —S(CH$_2$)$_t$(C$_6$-C$_{10}$ aryl), —O(CH$_2$)$_t$(C$_6$-C$_{10}$ aryl), and —(CH$_2$)$_t$(4-10 membered heterocyclic) groups are optionally fused to a C$_6$-C$_{10}$ aryl group, a C$_5$-C$_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing R$^{10}$ groups are optionally substituted by 1 to 3 substituents independently selected from nitro, trifluoromethyl, trifluoromethoxy, —NR$^6$SO$_2$R$^5$, —SO$_2$NR$^5$R$^6$, —NR$^6$C(O)R$^5$, —C(O)NR$^5$R$^6$, —NR$^5$R$^6$, —(CR$^6$R$^7$)$_m$OR$^6$ wherein m is an integer from 1 to 5, —OR$^5$ and the substituents listed in the definition of R$^5$ where R$^5$, R$^6$, and R$^7$ are as defined above with the proviso that R$^5$, R$^6$, and R$^7$ cannot be H, in a solvent, to give a compound of the Formula V. When X is a halogen or a sulfonate ester, a base is typically used. Non-limiting examples of a suitable base include alkali metal carbonates, alkali metal hydroxide, alkaline earth metal carbonate, alkaline earth metal hydroxide, alkali metal C$_1$-C$_4$ alkoxide, alkali metal hydride, and tertiary amines such as triethylamine, diisopropylethylamine, 1,8-diazabicyclo-[5.4.0]undec-7-ene ("DBU") and 1,5-Diazabicyclo-[4.3.0]non-5-ene ("DBN"). When X is an imidate, acids are typically used. Non-limiting examples include mineral acids such as hydrochloric acid and sulfuric acid, Bronsted acids such as triflic acid, or Lewis acids such as Trimethylsilyl trifluoromethane-sulfonate, transition metal chlorides (e.g., SnCl$_4$, TiCl$_4$), BF$_3$ etherate, and lanthanide triflate (e.g., Sc(OTf)$_3$ and Ln(OTf)$_3$). When X is hydroxyl, Mitsunobu reagents R'$_3$P and R"OC(O)OR" are preferably used. Preferred reagents are wherein R' is C$_1$-C$_4$ alkyl or C$_1$-C$_4$ aryl and R" is C$_1$-C$_4$ alkyl or C$_1$-C$_4$ aryl. More preferred reagents are wherein R' is phenyl and R" is ethyl or isopropyl.

The reaction may be carried out at a temperature of between about −20° C. to about 100° C., and preferably at between about 15° C. to about 35° C.

The reaction is also preferably carried out in the presence of a solvent. Preferably, when X is a halogen, sulfonate, or hydroxyl the solvent is a halogenated hydrocarbon solvent such as dichloromethane or chloroform, an ether, such as tetrahydrofuran, diisopropyl ether, methyl-tert-butyl ether, dioxane, or 2-methyltetrahydrofuran, or a dipolar aprotic solvent, such as dimethylsulfoxide, dimethylformamide, 1-methyl-2-pyrrolidinone, or dimethylacetamide. Preferably, when X is an imidate, the solvent is a polar solvent such as nitromethane, acetonitrile, or 2,2,2-trifluoroethanol or a halogenated hydrocarbon solvent such as dichloromethane or chloroform.

A preferred embodiment of the present invention refers to those processes wherein the compound of Formula VII is reacted with a compound of Formula VI in which X is an aryl sulfonate ester in a dipolar aprotic solvent with an alkali metal carbonate base to give a compound of the Formula V. It is especially preferred when R$^3$ is 2,6-difluoro-4-bromobenzyl; X is p-toluene sulfonate ester; R$^8$ is methyl; R$^9$ is methyl; n is 2; the alkali metal carbonate base is potassium carbonate; and the solvent is dimethylsulfoxide. This preferred process may be performed at about 15° C. to about 35° C.

In an especially preferred embodiment, the present invention refers to those processes wherein the compound of Formula V is 3-(4-Bromo-2,6-difluoro-benzyloxy)-5-methanesulfonyl-isothiazole-4-carboxylic acid methyl ester.

The invention also relates to compounds of Formulae IIa, IVa or Va that are useful in the preparation of the isothiazole derivatives of Formula I, which are in turn useful for binding or modulating KDR/FLK-1 receptors.

The present invention relates to a compound of the Formula IIa

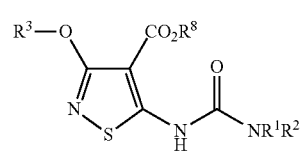

IIa or a pharmaceutically acceptable salt thereof; wherein

R$^1$ is H, C$_1$-C$_{10}$ alkyl, C$_2$-C$_{10}$ alkenyl, C$_2$-C$_{10}$ alkynyl, —C(O)(C$_1$-C$_{10}$ alkyl), —(CH$_2$)$_t$(C$_6$-C$_{10}$ aryl), —(CH$_2$)$_t$(4-10 membered heterocyclic), —C(O)(CH$_2$)$_t$(C$_6$-C$_{10}$ aryl), or —C(O)(CH$_2$)$_t$(4-10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic R$^1$ groups are optionally fused to a C$_6$-C$_{10}$ aryl group, a C$_5$-C$_8$ saturated cyclic group, or a 4-10 membered heterocyclic group; 1 or 2 carbon atoms in the foregoing heterocyclic moieties are optionally substituted by an oxo (=O) moiety; and the foregoing R$^1$ groups, except H, are optionally substituted by 1 to 3 R$^4$ groups;

R$^2$ is selected from the list of substituents provided in the definition of R$^1$, —SO$_2$(CH$_2$)$_t$(C$_6$-C$_{10}$ aryl), —SO$_2$(CH$_2$)$_t$(4-10 membered heterocyclic), and —OR$^5$, t is an integer ranging from 0 to 5, and the foregoing R$^2$ groups are optionally substituted by 1 to 3 R$^4$ groups;

or R$^1$ and R$^2$ may be taken together with the nitrogen to which each is attached to form a 4-10 membered saturated monocyclic or polycyclic ring or a 5-10 membered heteroaryl ring, wherein said saturated and heteroaryl rings optionally include 1 or 2 heteroatoms selected from O, S and —N(R$^6$)— in addition to the nitrogen to which R$^1$ and R$^2$ are attached, said —N(R$^6$)— is optionally =N— or —N= where R$^1$ and R$^2$ are taken together as said heteroaryl group, said saturated ring optionally may be partially unsaturated by including 1 or 2 carbon-carbon double bonds, and said saturated and heteroaryl rings, including the R$^6$ group of said —N(R$^6$)—, are optionally substituted by 1 to 3 R$^4$ groups;

R$^3$ is H, C$_1$-C$_{10}$ alkyl, C$_2$-C$_{10}$ alkenyl, C$_2$-C$_{10}$ alkynyl, —(CH$_2$)$_t$(C$_6$-C$_{10}$ aryl), or —(CH$_2$)$_t$(4-10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic R$^3$ groups are optionally fused to a C$_6$-C$_{10}$ aryl group, a C$_5$-C$_8$ saturated cyclic group, or a 4-10 membered heterocyclic group; 1 or 2 carbon atoms in the foregoing heterocyclic moieties are optionally substituted by an oxo (=O) moiety; the —(CH$_2$)$_t$— moieties of the foregoing R$^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R^5$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_tOR^6$, —$(CH_2)_t(C_6$-$C_{10}$ aryl), —$SO_2(CH_2)_t(C_6$-$C_{10}$ aryl), —$S(CH_2)_t(C_6$-$C_{10}$ aryl), —$O(CH_2)_t(C_6$-$C_{10}$ aryl), —$(CH_2)_t$(4-10 membered heterocyclic), and —$(CR^6R^7)_mOR^6$, wherein m is an integer from 1 to 5 and t is an integer from 0 to 5; said alkyl group optionally contains 1 or 2 hetero moieties selected from O, S and —N($R^6$)— with the proviso that two O atoms, two S atoms, or an O and S atom are not attached directly to each other; said aryl and heterocyclic $R^4$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing $R^4$ groups are optionally substituted by 1 to 3 substituents independently selected from nitro, trifluoromethyl, trifluoromethoxy, azido, —$NR^6SO_2R^5$, —$SO_2NR^5R^6$, —$NR^6C(O)R^5$, —$C(O)NR^5R^6$, —$NR^5R^6$, —$(CR^6R^7)_mOR^6$ wherein m is an integer from 1 to 5, —$OR^5$ and the substituents listed in the definition of $R^5$;

each $R^5$ is independently selected from H, $C_1$-$C_{10}$ alkyl, —$(CH_2)_t(C_6$-$C_{10}$ aryl), and —$(CH_2)_t$(4-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^5$ groups are optionally fused to a $C_6$-$C_{10}$ aryl group, a $C_5$-$C_8$ saturated cyclic group, or a 4-10 membered heterocyclic group; and the foregoing $R^5$ substituents, except H, are optionally substituted by 1 to 3 substituents independently selected from nitro, trifluoromethyl, trifluoromethoxy, azido, —$NR^6C(O)R^7$, —$C(O)NR^6R^7$, —$NR^6R^7$, hydroxy, $C_1$-$C_6$ alkyl, and $C_1$-$C_6$ alkoxy;

each $R^6$ and $R^7$ is independently H or $C_1$-$C_6$ alkyl; and $R^8$ is H, $C_1$-$C_{10}$ alkyl, —$C(O)(C_1$-$C_{10}$ alkyl), —$C(O)(C_6$-$C_{10}$ aryl), —$C(O)$(4-10 membered heterocyclic), —$(CH_2)_t(C_6$-$C_{10}$ aryl), —$(CH_2)_t$(4-10 membered heterocyclic), —$C(O)O(C_1$-$C_{10}$ alkyl); —$C(O)O(C_6$-$C_{10}$ aryl), —$C(O)O$(4-10 membered heterocyclic), wherein t is an integer from 0 to 5; said aryl and heterocyclic $R^8$ groups are optionally fused to a $C_6$-$C_{10}$ aryl group; and the foregoing aryl and heterocyclic $R^8$ groups are optionally substituted with 1-2 substituents independently selected from halogen, trifluoromethyl, $C_1$-$C_6$ alkoxy, $C_1$-$C_6$ alkyl, and nitro groups with the proviso that $R^8$ is not ethyl when simultaneously $R^1$ is H, $R^2$ is pyrrolidin-1-yl-butyl and $R^3$ is $C_1$-$C_3$ alkyl.

An embodiment of the present invention refers to the compounds of Formula IIa where $R^2$ is H and $R^1$ is $C_1$-$C_{10}$ alkyl optionally substituted by 1 or 2 substituents independently selected from —$NR^5R^6$, —$NR^5(CR^6R^7)_tOR^6$ and —$(CH_2)_t$(4-10 membered heterocyclic) where t is an integer from 0 to 5. In another embodiment $R^1$ is selected from propyl, butyl, pentyl and hexyl, and may be optionally substituted with dimethylamino, hydroxy, pyrrolidinyl, morpholino, and ethyl-(2-hydroxy-ethyl)-amino, and $R^2$ is H.

In another embodiment the present invention refers to the compounds of Formula IIa where $R^2$ is H and $R^1$ is —$(CH_2)_t$(4-10 membered heterocyclic) wherein t is an integer from 0 to 5, said heterocyclic group is optionally fused to a $C_6$-$C_{10}$ aryl group, a $C_5$-$C_8$ saturated cyclic group, or a 4-10 membered heterocyclic group and the $R^1$ group, including any fused portions of said $R^1$ group, may be substituted by 1 or 2 substituents independently selected from $C_1$-$C_4$ alkyl, hydroxy and hydroxymethyl. In this embodiment, preferably the 4-10 membered heterocyclic of $R^1$ is selected from one of morpholino, pyrrolidinyl, imidazolyl, piperazinyl, piperidinyl, and 2,5-diaza-bicyclo[2.2.1]hept-2-yl and the $R^1$ group is optionally substituted with hydroxy, hydroxymethyl and methyl, and the t variable of the $R^1$ group ranges from 2-5.

An embodiment of the present invention refers to the compounds of Formula IIa wherein $R^3$ is —$(CH_2)_t(C_6$-$C_{10}$ aryl) wherein t is an integer from 1 to 3 and the $R^3$ group is optionally substituted with 1 to 4 $R^4$ groups. In this embodiment, preferably $R^3$ is benzyl optionally substituted by 1 to 4 halo substituents.

In a preferred embodiment, the present invention refers to compounds of Formula IIa wherein $R^2$ is H, $R^1$ is —$(CH_2)_4$-1-pyrrolidine, $R^3$ is 2,6-difluoro-4-bromobenzyl, and $R^8$ is methyl.

Another embodiment of the present invention refers to the compounds of Formula IVa

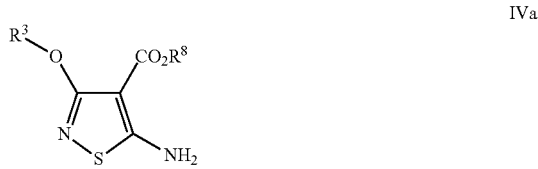

or a pharmaceutically acceptable salt thereof; wherein $R^3$ is H, $C_1$-$C_{10}$ alkyl, $C_2$-$C_{10}$ alkenyl, $C_2$-$C_{10}$ alkynyl, —$(CH_2)_t(C_6$-$C_{10}$ aryl), or —$(CH_2)_t$(4-10 membered heterocyclic), wherein t is an integer from 0 to 5; said alkyl group optionally includes 1 or 2 hetero moieties selected from O, S and —N($R^6$)— with the proviso that two O atoms, two S atoms, or an O and S atom are not attached directly to each other; said aryl and heterocyclic $R^3$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; the —$(CH_2)_t$— moieties of the foregoing $R^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from halo, $C_1$-$C_{10}$ alkyl, $C_2$-$C_{10}$ alkenyl, $C_2$-$C_{10}$ alkynyl, nitro, trifluoromethyl, trifluoromethoxy, azido, —$OR^5$, —$NR^6C(O)OR^5$, —$NR^6SO_2R$, —$SO_2NR^5R^6$, —$NR^6C(O)R^5$, —$C(O)NR^5R^6$, —$NR^5R^6$, —$S(O)_jR^7$ wherein j is an integer ranging from 0 to 2, —$NR^5(CR^6R^7)_tOR^6$, —$(CH_2)_t(C_6$-$C_{10}$ aryl), —$SO_2(CH_2)_t(C_6$-$C_{10}$ aryl), —$S(CH_2)_t(C_6$-$C_{10}$ aryl), —$O(CH_2)_t(C_6$-$C_{10}$ aryl), —$(CH_2)_t$(4-10 membered heterocyclic), and —$(CR^6R^7)_mOR^6$, wherein m is an integer from 1 to 5 and t is an integer from 0 to 5; said alkyl group optionally contains 1 or 2 hetero moieties selected from O, S and —N($R^6$)— with the proviso that two O atoms, two S atoms, or an O and S atom are not attached directly to each other; said aryl and heterocyclic $R^4$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing $R^4$ groups are optionally substituted by 1 to 3 substituents independently selected from nitro, trifluoromethyl, trifluoromethoxy, azido, —NR⁶SO₂R⁵, —SO₂NR⁵R⁶, —NR⁶C(O)R⁵, —C(O)NR⁵R⁶, —NR⁵R⁶, —(CR⁶R⁷)$_m$OR⁶ wherein m is an integer from 1 to 5, —OR⁵ and the substituents listed in the definition of R⁵;

each R⁵ is independently selected from H, $C_1$-$C_{10}$ alkyl, —(CH₂)$_t$($C_6$-$C_{10}$ aryl), and —(CH₂)$_t$(4-10 membered heterocyclic), wherein t is an integer from 0 to 5; said alkyl group optionally includes 1 or 2 hetero moieties selected from O, S and —N(R⁶)— with the proviso that two O atoms, two S atoms, or an O and S atom are not attached directly to each other; said aryl and heterocyclic R⁵ groups are optionally fused to a $C_6$-$C_{10}$ aryl group, a $C_5$-$C_8$ saturated cyclic group, or a 4-10 membered heterocyclic group; and the foregoing R⁵ substituents, except H, are optionally substituted by 1 to 3 substituents independently selected from nitro, trifluoromethyl, trifluoromethoxy, azido, —NR⁶C(O)R⁷, —C(O)NR⁶R⁷, —NR⁶R⁷, hydroxy, $C_1$-$C_6$ alkyl, and $C_1$-$C_6$ alkoxy;

each R⁶ and R⁷ is independently H or $C_1$-$C_6$ alkyl; and

R⁸ is H, $C_1$-$C_{10}$ alkyl, —C(O)($C_1$-$C_{10}$ alkyl), —C(O)($C_6$-$C_{10}$ aryl), —C(O)(4-10 membered heterocyclic), —(CH₂)$_t$($C_6$-$C_{10}$ aryl), —(CH₂)$_t$(4-10 membered heterocyclic), —C(O)O($C_1$-$C_{10}$ alkyl); —C(O)O($C_6$-$C_{10}$ aryl), —C(O)O(4-10 membered heterocyclic), wherein t is an integer from 0 to 5; said aryl and heterocyclic R⁸ groups are optionally fused to a $C_6$-$C_{10}$ aryl group; and the foregoing aryl and heterocyclic R⁸ groups are optionally substituted with 1-2 substituents independently selected from halogen, trifluoromethyl, $C_1$-$C_6$ alkoxy, $C_1$-$C_6$ alkyl, and nitro groups with the proviso that R⁸ is not ethyl when R³ is $C_1$-$C_3$ alkyl.

In a preferred compound of Formula IVa, R³ is —(CH₂)$_t$($C_6$-$C_{10}$ aryl), wherein t is an integer from 1 to 3 and R³ is optionally substituted by 1 to 4 R⁴ groups, and more preferred R³ is benzyl substituted by 1 to 4 halo substituents.

In a preferred embodiment, the present invention refers to compounds of Formula IVa wherein R³ is 2,6-difluoro-4-bromobenzyl, and R⁸ is methyl.

Another embodiment of the present invention refers to the compounds of Formula Va

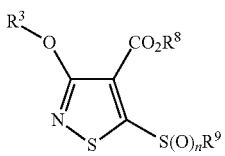

Va or a pharmaceutically acceptable salt thereof; wherein

R³ is $C_1$-$C_{10}$ alkyl, $C_2$-$C_{10}$ alkenyl, $C_2$-$C_{10}$ alkynyl, —(CH₂)$_t$($C_6$-$C_{10}$ aryl), or —(CH₂)$_t$(4-10 membered heterocyclic), wherein t is an integer from 0 to 5; said alkyl group optionally includes 1 or 2 hetero moieties selected from O, S and —N(R⁶)— with the proviso that two O atoms, two S atoms, or an O and S atom are not attached directly to each other; said aryl and heterocyclic R³ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; the —(CH₂)$_t$— moieties of the foregoing R³ groups optionally include a carbon-carbon double or triple bond where t is an integer from 2 to 5, and the foregoing R³ groups are optionally substituted by 1 to 5 R⁴ groups;

each R⁴ is independently selected from halo, $C_1$-$C_{10}$ alkyl, $C_2$-$C_{10}$ alkenyl, $C_2$-$C_{10}$ alkynyl, nitro, trifluoromethyl, trifluoromethoxy, azido, —OR⁵, —NR⁶C(O)OR⁵, —NR⁶SO₂R⁵, —SO₂NR⁵R⁶, —NR⁶C(O)R⁵, —C(O)NR⁵R⁶, —NR⁵R⁶, —S(O)$_j$R⁷ wherein j is an integer ranging from 0 to 2, —NR⁵(CR⁶R⁷)$_t$OR⁶, —(CH₂)$_t$($C_6$-$C_{10}$ aryl), —SO₂(CH₂)$_t$($C_6$-$C_{10}$ aryl), —S(CH₂)$_t$($C_6$-$C_{10}$ aryl), —O(CH₂)$_t$($C_6$-$C_{10}$ aryl), —(CH₂)$_t$(4-10 membered heterocyclic), and —(CR⁶R⁷)$_m$OR⁶, wherein m is an integer from 1 to 5 and t is an integer from 0 to 5; said alkyl group optionally contains 1 or 2 hetero moieties selected from O, S and —N(R⁶)— with the proviso that two O atoms, two S atoms, or an O and S atom are not attached directly to each other; said aryl and heterocyclic R⁴ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing R⁴ groups are optionally substituted by 1 to 3 substituents independently selected from nitro, trifluoromethyl, trifluoromethoxy, azido, —NR⁶SO₂R⁵, —SO₂NR⁵R⁶, —NR⁶C(O)R⁵, —C(O)NR⁵R⁶, —NR⁵R⁶, —(CR⁶R⁷)$_m$OR⁶ wherein m is an integer from 1 to 5, —OR⁵ and the substituents listed in the definition of R⁵;

each R⁵ is independently selected from H, $C_1$-$C_{10}$ alkyl, —(CH₂)$_t$($C_6$-$C_{10}$ aryl), and —(CH₂)$_t$(4-10 membered heterocyclic), wherein t is an integer from 0 to 5; said alkyl group optionally includes 1 or 2 hetero moieties selected from O, S and —N(R⁶)— with the proviso that two O atoms, two S atoms, or an O and S atom are not attached directly to each other; said aryl and heterocyclic R⁵ groups are optionally fused to a $C_6$-$C_{10}$ aryl group, a $C_5$-$C_8$ saturated cyclic group, or a 4-10 membered heterocyclic group; and the foregoing R⁵ substituents, except H, are optionally substituted by 1 to 3 substituents independently selected from nitro, trifluoromethyl, trifluoromethoxy, azido, —NR⁶C(O)R⁷, —C(O)NR⁶R⁷, —NR⁶R⁷, hydroxy, $C_1$-$C_6$ alkyl, and $C_1$-$C_6$ alkoxy;

each R⁶ and R⁷ is independently H or $C_1$-$C_6$ alkyl;

R⁸ is H, $C_1$-$C_{10}$ alkyl, —C(O)($C_1$-$C_{10}$ alkyl), —C(O)($C_6$-$C_{10}$ aryl), —C(O)(4-10 membered heterocyclic), —(CH₂)$_t$($C_6$-$C_{10}$ aryl), —(CH₂)$_t$(4-10 membered heterocyclic), —C(O)O($C_1$-$C_{10}$ alkyl); —C(O)O($C_6$-$C_{10}$ aryl), —C(O)O(4-10 membered heterocyclic), wherein t is an integer from 0 to 5; said aryl and heterocyclic R⁸ groups are optionally fused to a $C_6$-$C_{10}$ aryl group; and the foregoing aryl and heterocyclic R⁸ groups are optionally substituted with 1-2 substituents independently selected from halogen, trifluoromethyl, $C_1$-$C_6$ alkoxy, $C_1$-$C_6$ alkyl, and nitro groups;

R⁹ is $C_1$-$C_{10}$ alkyl, $C_6$-$C_{10}$ aryl, 4-10 membered heterocyclic, the aryl and heterocyclic R⁹ groups are optionally fused to a $C_6$-$C_{10}$ aryl group; and the foregoing aryl and heterocyclic R⁹ groups are optionally substituted independently with 1-2 substituents independently selected from halogen, trifluoromethyl, $C_1$-$C_6$ alkoxy, $C_1$-$C_6$ alkyl, and nitro groups; and n is 1 or 2.

In a preferred compound of Formula Va, R³ is —(CH₂)$_t$($C_6$-$C_{10}$ aryl), wherein t is an integer from 1 to 3 and the R³ group is optionally substituted by 1 to 4 R⁴ groups, and more preferably R³ is benzyl optionally substituted by 1 to 4 halo substituents, still more preferably R⁸ and R⁹ are methyl.

In a still more preferred embodiment, the present invention refers to compounds of Formula Va wherein n is 2, R³ is 2,6-difluoro-4-bromobenzyl, R⁸ is methyl, and R⁹ is methyl.

In an embodiment, the compound of the Formula I, as defined previously, is prepared by reacting the compound of Formula IIa with an ammonia source in a solvent.

In another embodiment, the compound of the Formula II, as defined previously, is prepared by reacting a compound of the Formula IVa with a source of carbonyl with or without an added base, and then adding a compound of Formula III, as previously defined, in a solvent or alternatively, reacting a compound of Formula III with a source of carbonyl with or without an added base, and then adding a compound of Formula IVa in a solvent to give a compound of the Formula II.

In yet another embodiment, the compound of the Formula IV, as defined previously, is prepared by reacting a compound of Formula Va with an ammonia source in a solvent.

In this invention, the term "halo," unless otherwise indicated, includes fluoro, chloro, bromo or iodo. Preferred halo groups are fluoro, chloro and bromo.

The term "alkyl," as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl," as used herein, unless otherwise indicated, includes monovalent hydrocarbon radicals having at least one carbon-carbon double bond and also having straight, cyclic or branched moieties as provided above in the definition of "alkyl."

The term "alkynyl," as used herein, unless otherwise indicated, includes monovalent hydrocarbon radicals having at least one carbon-carbon triple bond and also having straight, cyclic or branched moieties as provided above in the definition of "alkyl."

The term "alkoxy," as used herein, unless otherwise indicated, includes O-alkyl groups wherein "alkyl" is as defined above.

The term "aryl," as used herein, unless otherwise indicated, includes an organic radical derived from an aromatic hydrocarbon by removal of one hydrogen, such as phenyl or naphthyl.

The term "heteroaryl," as used herein, unless otherwise indicated, includes an organic radical derived by removal of one hydrogen atom from a carbon atom in the ring of a heteroaromatic hydrocarbon, containing one or more heteroatoms independently selected from O, S, and N. Heteroaryl groups must have at least 5 atoms in their ring system and are optionally substituted independently with 0-2 halogen, trifluoromethyl, $C_1$-$C_6$ alkoxy, $C_1$-$C_6$ alkyl, or nitro groups.

The term "4-10 membered heterocyclic," as used herein, unless otherwise indicated, includes aromatic and non-aromatic heterocyclic groups containing one or more heteroatoms each selected from O, S and N, wherein each heterocyclic group has from 4-10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, $^3$H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "saturated cyclic group" as used herein, unless otherwise indicated, includes non-aromatic, fully saturated cyclic moieties wherein alkyl is as defined above.

The phrase "pharmaceutically acceptable salt(s)", as used herein, unless otherwise indicated, includes salts of acidic or basic groups which may be present in the compounds of the invention. The compounds of the invention that are basic in nature are capable of forming a wide variety of salts with various inorganic and organic acids. The acids that may be used to prepare pharmaceutically acceptable acid addition salts of such basic compounds of the invention are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Those compounds of the invention that are acidic in nature are capable of forming base salts with various pharmacologically acceptable cations. Examples of such salts include the alkali metal or alkaline earth metal salts and particularly the sodium and potassium salts.

The term "solvate," as used herein includes a compound of the invention or a salt thereof, that further includes a stoichiometric or non-stoichiometric amount of a solvent bound by non-covalent intermolecular forces. Preferred solvents are volatile, non-toxic, and/or acceptable for topical administration to humans.

The term "hydrate," as used herein refers to a compound of the invention or a salt thereof, that further includes a stoichiometric or non-stoichiometric amount of water bound by non-covalent intermolecular forces.

Certain compounds of the present invention may have asymmetric centers and therefore appear in different enantiomeric forms. This invention relates to the use of all optical isomers and stereoisomers of the compounds of the invention and mixtures thereof. The compounds of the invention may also appear as tautomers. This invention relates to the use of all such tautomers and mixtures thereof.

The subject invention also includes isotopically-labelled compounds, and the pharmaceutically acceptable salts thereof, which are identical to those recited in Formulas I, II, IIa, IV, IVa, V and Va but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

Compounds of Formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

Each of the patents, patent applications, published International applications, and scientific publications referred to in this patent application is incorporated herein by reference in its entirety.

DETAILED DESCRIPTION OF THE INVENTION

The compounds of Formula I are useful as agents for binding or modulating KDR/FLK-1 receptors and are thus useful in the treatment of hyperproliferative diseases, such as cancers in mammals.

The process of the present invention in its first aspect concerns preparing the isothiazole derivatives of Formula I. Compounds of the Formula I may be prepared according to the following reaction scheme and discussion. Unless otherwise indicated, $R^1$, $R^2$, $R^3$, $R^4$, $R^5$, $R^6$, $R^7$, $R^8$, $R^9$ and $R^{10}$ in the reaction scheme and discussion that follow are as defined above.

SCHEME 1

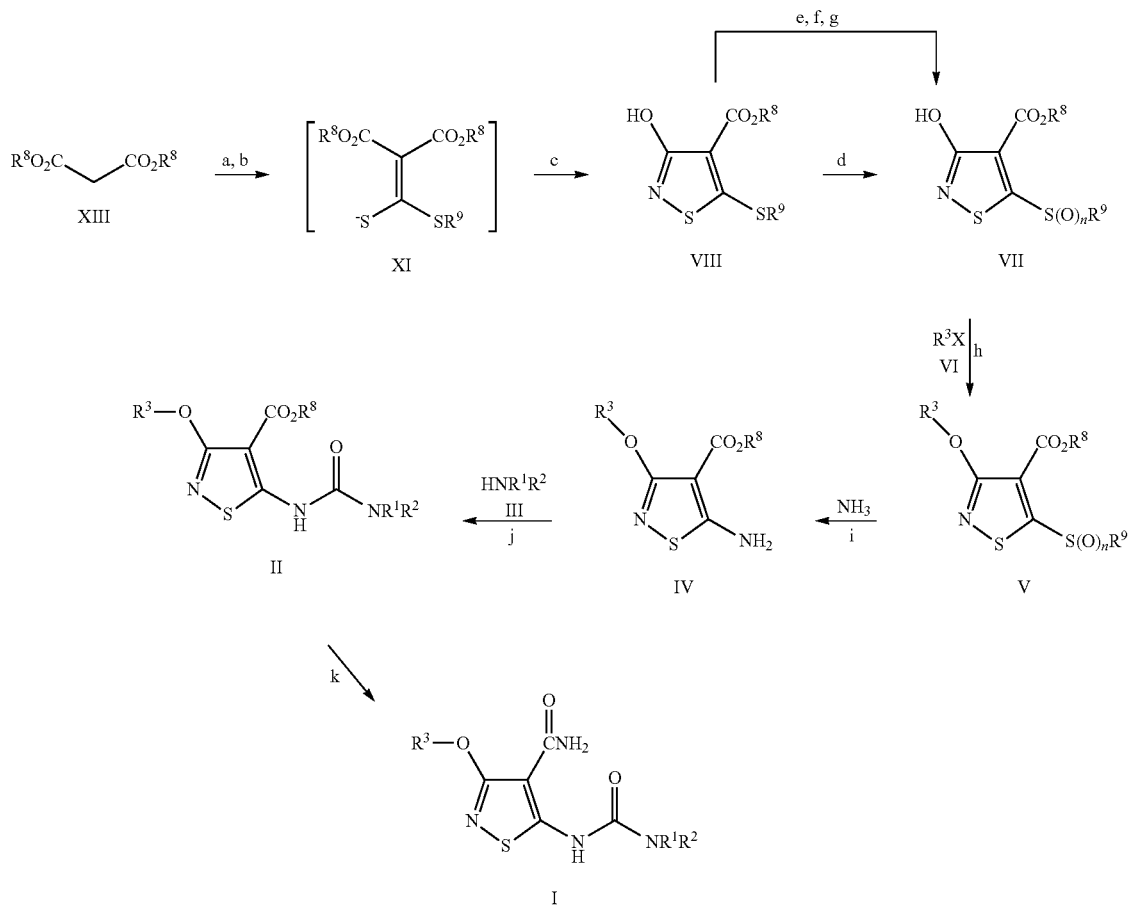

With reference to Scheme 1 above, the compound of Formula I may be prepared by treating a malonate diester (XIII) with base and carbon disulfide (reaction a), followed by treatment with an alkylating agent to provide an (alkyl)sulfanyl-ethenethiol anion (XI) (reaction b). Amination of the (alkyl) sulfanyl-ethenethiol anion via an electrophilic aminating agent yields the 5-(alkyl)sulfanyl isothiazole (VIII) (reaction c). Oxidation of the isothiazole (VIII) with an oxidizing agent in a suitable solvent yields either the 5-(alkyl)sulfonyl isothiazole when n=2; or 5-(alkyl)sulfinyl isothiazole when n=1 (VII) (reaction d). Alternatively, the isothiazole, VIII, may be protected with a suitable protecting group (PG) to give a compound of general Formula X (reaction e), which may then be treated with an oxidizing agent in a suitable solvent to prepare compounds of general Formula IX (reaction f). Compounds of general formula IX may then be deprotected to give compounds of 5-(alkyl)sulfonyl (or sulfinyl) isothiazole, VII. This mechanism is illustrated in Scheme 2 below.

SCHEME 2

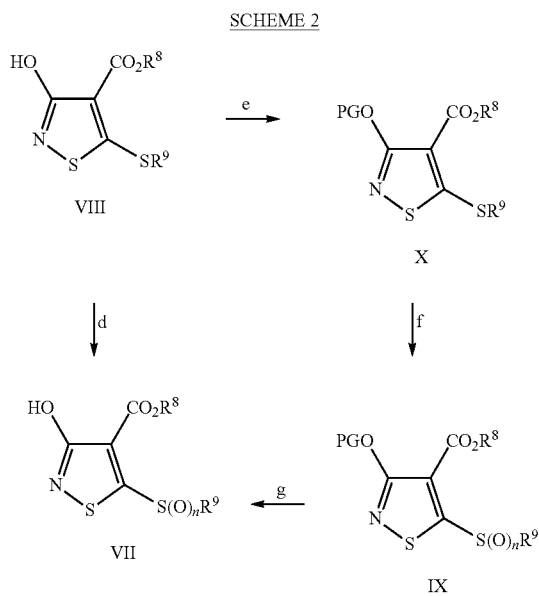

Referring back to Scheme 1, the 5-(alkyl)sulfonyl/sulfinyl isothiazole VII is treated with a compound of general formula $R^3X$ (VI), typically under basic conditions, to yield an isothiazole (V) now having alkoxy functionality at position three (3) of the isothiazole (reaction h). This reaction is particularly and unexpectedly advantageous when compound VI is a tosylate and the conditions include a base in a dipolar aprotic solvent. The reaction under these conditions proceeds in unusually high O:N selectivity where alkylation takes place on the hydroxyl group instead of the nitrogen atom of the isothiazole ring. Under the appropriate conditions O:N selectivity approximates a ratio of 35:1 O:N selectivity.

Alkylations of a variety of substituted 3-hydroxyisothiazoles have been reported in the literature. Mixtures of O- and N-alkylated products were observed in all cases, with a wide variety of electrophiles (alkyl halides, alkyl sulfates, diazomethane), solvents (water, acetone, DMSO, DMF, MeCN, DME) and bases (NaOH, $K_2CO_3$, $Li_2CO_3$, $Ag_2CO_3$) being used. For example, a thorough study on the alkylation of 3-hydroxyisothiazole is reported in Tetrahedron, 1970, (26), 2497-2506:

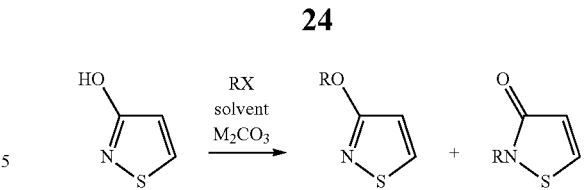

| RX | M | DMSO (O:N) | DMF (O:N) | MeCN (O:N) | DME (O:N) |
|---|---|---|---|---|---|
| MeI | K | 46:54 | 41:59 | 40:60 | 20:80 |
|  | Ag | 68:32 | — | — | — |
|  | Li | 34:66 | 17:83 | — | — |
| EtI | K | 25:25 | 77:23 | 70:30 | 50:50 |
|  | Li | — | 55:45 | — | — |
| PrBr | K | 78:22 | 80:20 | 80:20 | — |
| iPrBr | K | 88:12 | — | 86:14 | — |
| BnCl | K | 68:32 | 59:41 | 45:55 | 34:66 |

Additional references demonstrating 3-hydroxyisothiazole alkylation reactions with low O:N selectivity include the following:

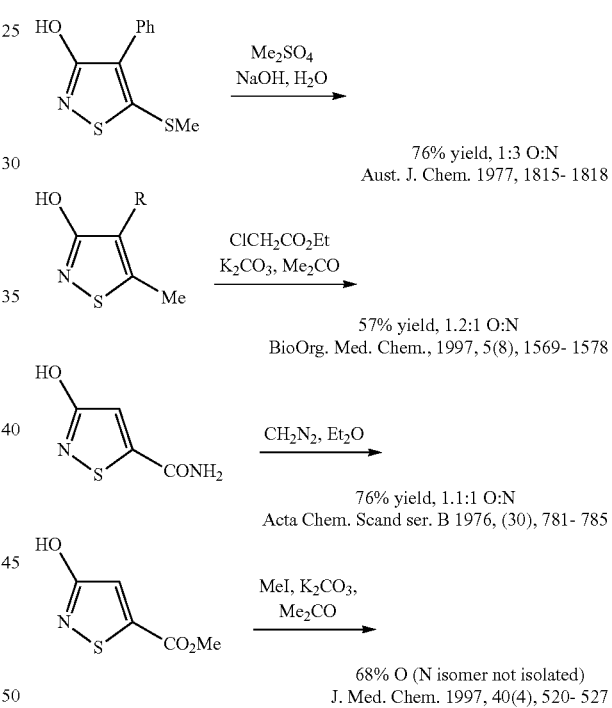

The alkylation step (reaction h) in the process of the present invention proceeds with very high O:N selectivity, namely, approximately 35:1 for the conditions described in the experimental procedure of Example seven (7) discussed below, which is much higher than the selectivity ratios published in the references cited herein.

Referring again to Scheme 1, the alkoxylated isothiazole (V) is treated with a source of ammonia in a suitable solvent converting the sulfonyl/sulfinyl moiety at position five (5) of the isothiazole to a primary amine (IV) (reaction i). A compound of general Formula IV may be combined with a secondary amine and a carbonyl source, with or without an added base, in a suitable solvent to give the compound of general Formula II, replacing the primary amine with ureido functionality at position five (5) on the isothiazole. A second treatment with an ammonia source converts the alkyl ester to an amide providing the compound of general Formula I.

The starting materials employed in Scheme I are readily commercially available or readily prepared using methods well known in the art.

In each of the reactions discussed or illustrated in the Schemes, pressure is not critical unless otherwise indicated. Pressures from about 0.5 atmospheres to about 5 atmospheres are generally acceptable, and ambient pressure, i.e., about 1 atmosphere, is preferred as a matter of convenience.

The examples and preparations provided below further illustrate and exemplify the compounds of the present invention, methods of preparing such compounds, and the methods of the present invention. It is to be understood that the scope of the present invention is not limited in any way by the scope of the following examples and preparations.

In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The present invention is illustrated by the following Examples. It will be understood, however, that the invention is not limited by the specific details of the following Examples.

Example 1

Preparation of 2,2-Bis-methoxycarbonyl-1-methylsulfanyl-ethenethiol anion

MeO₂C⎯⎯CO₂Me $\xrightarrow[\text{5-25° C.}]{\text{DBU, CS}_2, \text{Me}_2\text{SO}_4 \atop \text{CH}_3\text{CN}}$

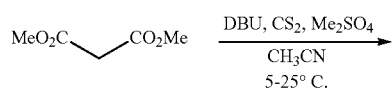

A reaction vessel was charged with acetonitrile (240 mL, 6 volumes) followed by 1,8-diazabicyclo-[5.4.0]undec-7-ene (2.1 equivalents, 96.8 g). The mixture was cooled to 5° C. under nitrogen atmosphere. Dimethyl malonate (1.0 equiv, 40.0 g) was added over 10-15 minutes. The mixture was held for 30-45 minutes at 5° C. Carbon disulfide (1.0 equiv, 23.1 g) was added over 10-15 minutes, and then the mixture was held for 60-70 minutes at 5° C. Dimethyl sulfate (1.05 equiv, 40.1 g) was added over 10-15 minutes, and then the mixture was held at 5° C. for 16 hours. The mixture containing 2,2-Bis-methoxycarbonyl-1-methylsulfanyl-ethenethiol anion was finally warmed to 25° C. over 30 minutes, and held at 25° C. for 1-2 hours.

Example 2

Preparation of 3-Hydroxy-5-methylsulfanyl-isothiazole-4-carboxylic acid methyl ester

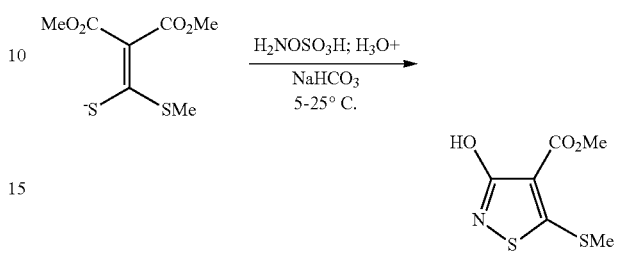

A separate reaction vessel was charged with water (280 mL, 7 volumes) and sodium hydrogencarbonate (1.5 equiv, 38.2 g). The water/sodium hydrogencarbonate mixture was cooled to 5° C. under nitrogen atmosphere. Hydroxylamine-O-sulfonic acid (1.2 equiv, 41.1 g) was added over 5 minutes, and the mixture was stirred 15-30 minutes. The 2,2-Bis-methoxycarbonyl-1-methylsulfanyl-ethenethiol anion/acetonitrile solution from Example 1 was added over 60-70 minutes. The mixture was warmed to 25° C. over 1 hour, then held for 16 hours at 25° C. Most of the acetonitrile was removed by vacuum distillation (130 Torr, 50° C.). The residue was cooled to room temperature, acidified to pH ~1 by addition of 37% hydrochloric acid (32 mL). The solids were granulated for 16 hours at 25° C. The slurry was filtered, and the filter cake was washed 3×100 mL with water, once with 200 mL 1:3 ethyl acetate:hexanes (v/v), and once with 100 mL 1:3 ethyl acetate:hexanes (v/v). The wet cake (50.5 g) was dried in a vacuum oven for 16 hours to give 3-Hydroxy-5-methylsulfanyl-isothiazole-4-carboxylic acid methyl ester, providing 45.4 grams (73% yield). ¹H NMR: (DMSO-d₆) δ 11.92 (s, 1H); 3.74 (s, 3H); 2.53 (s, 3H). MS: (API-ES pos) 206 (M+H)⁺, base.

Example 3

Preparation of 3-Methoxycarbonyloxy-5-methylsulfanyl-isothiazole-4-carboxylic acid methyl ester

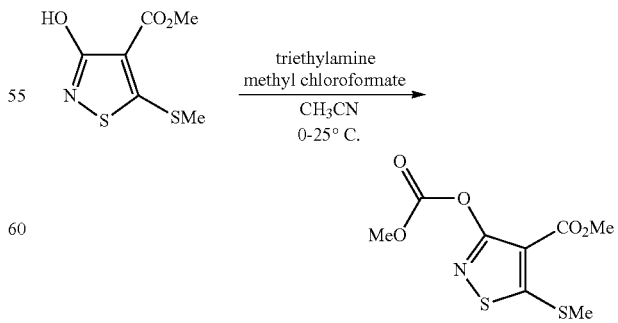

3-Hydroxy-5-methylsulfanyl-isothiazole-4-carboxylic acid methyl ester (1.00 equiv, 10.0 g) and dichloromethane (100 mL, 10 volumes) were charged to a flask and held at 25° C. under nitrogen atmosphere. Triethylamine (1.0 equiv, 6.78 mL, 4.88 g) was added. An orange solution formed, which was cooled to 0° C. Methyl chloroformate (1.0 equiv, 3.74 mL, 4.56 g) was added over 3 minutes. The mixture stirred at 25° C. for 2 hours, then was washed with water (50 mL, 5 volumes) then brine (50 mL, 5 volumes). The solvent was displaced with acetonitrile (100 mL, 10 volumes) to give a tan slurry containing 3-Methoxycarbonyloxy-5-methylsulfanyl-isothiazole-4-carboxylic acid methyl ester.

Example 4

Preparation of 5-Methanesulfonyl-3-methoxycarbonyloxy-isothiazole-4-carboxylic acid methyl ester

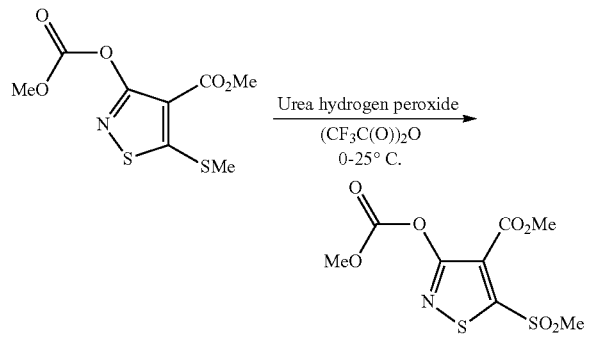

The 3-Methoxycarbonyloxy-5-methylsulfanyl-isothiazole-4-carboxylic acid methyl ester slurry was cooled to 0° C., and urea hydrogen peroxide addition compound (2.8 equiv, 12.8 g) was added. Trifluoroacetic acid anhydride (2.8 equiv, 19.2 mL, 28.4 g) was added dropwise over 20 minutes. The mixture stirred at 0° C. for 45 minutes, and quenched with sodium hydrogen sulfite (2.0 equiv, 10.0 g) in water (90 mL, 9 volumes) and stirred at 25° C. Most of the acetonitrile was removed under vacuum, then the aqueous residue was extracted once with 100 mL and once again with 50 mL dichloromethane to provide 5-Methanesulfonyl-3-methoxycarbonyloxy-isothiazole-4-carboxylic acid methyl ester.

Example 5

Preparation of 3-Hydroxy-5-methanesulfonyl-isothiazole-4-carboxylic acid methyl ester

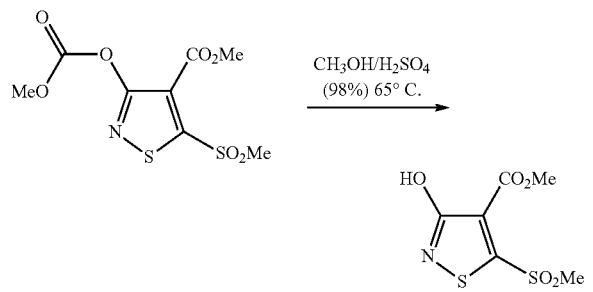

The 5-Methanesulfonyl-3-methoxycarbonyloxy-isothiazole-4-carboxylic acid methyl ester/dichloromethane extracts were combined, then displaced with methanol (150 mL, 15 volumes). A solution of 98% sulfuric acid (50 mL, 5 volumes) in water (100 mL, 10 volumes) was added and the mixture was heated at 65° C. for 6 hours. The foamy slurry became a clear solution with some insoluble white solids over time. The mixture was cooled to 25° C. and stirred for 16 hours. Most of the methanol was removed under vacuum. The aqueous residue was extracted once with 100 mL dichloromethane, then twice with 50 mL dichloromethane. The combined dichloromethane extracts were dried over anhydrous magnesium sulfate and filtered. The dichloromethane was displaced with hexanes (100 mL, 10 volumes) and stirred at 25° C. until solids formed. The solids were filtered, and the filter cake was rinsed with hexane and dried to give 9.27 g of 3-Hydroxy-5-methanesulfonyl-isothiazole-4-carboxylic acid methyl ester (80% yield). $^1$H NMR (DMSO-$d_6$): δ 13.07 (s, 1H); 3.83 (s, 3H); 3.55 (s, 3H). MS (API-ES pos): 238 (M+H)+; 206 (M−MeO)+, base.

Example 6

Preparation of Toluene-4-sulfonic acid 4-bromo-2,6-difluoro-benzyl ester

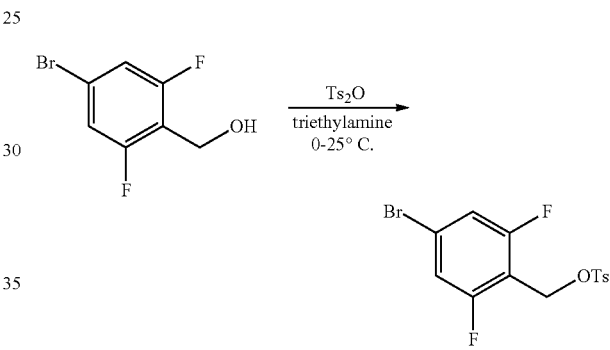

In a flask under nitrogen (4-Bromo-2,6-difluoro-phenyl)-methanol (1.10 equiv, 19.1 g) was taken up in dichloromethane (185 mL, 10 volumes) and p-toluenesulfonic anhydride (1.1 equiv, 28.9 g) was added. The mixture was cooled to 0° C. and triethylamine (1.2 equiv, 13.0 mL, 9.47 g) was added dropwise over 20 minutes. The mixture was warmed to 25° C. and stirred for one hour. The mixture was then washed once with 185 mL 1N hydrochloric acid, then once with 92.5 mL 1N hydrochloric acid. The organic layer, containing toluene-4-sulfonic acid 4-bromo-2,6-difluoro-benzyl ester, was concentrated to about 55-60 mL.

Example 7

Preparation of 3-(4-Bromo-2,6-difluoro-benzyloxy)-5-methanesulfonyl-isothiazole-4-carboxylic acid methyl ester

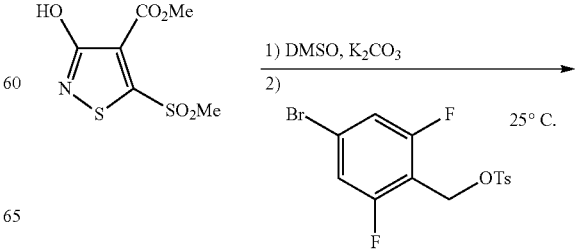

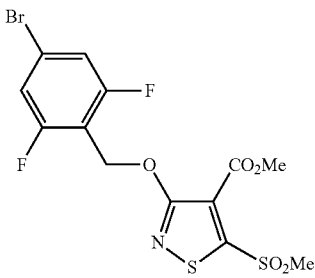

In a separate vessel, 3-Hydroxy-5-methanesulfonyl-isothiazole-4-carboxylic acid methyl ester (1.00 equiv, 18.5 g) was taken up in dimethylsulfoxide (185 mL, 10 volumes) and potassium carbonate (1.0 equiv, 10.8 g) was added. The toluene-4-sulfonic acid 4-bromo-2,6-difluoro-benzyl ester/dichloromethane solution from Example 6 was added to the 3-Hydroxy-5-methanesulfonyl-isothiazole-4-carboxylic acid methyl/potassium carbonate/dimethylsulfoxide slurry dropwise over 1 hour. The mixture was stirred at 25° C. for 16.5 hours. Dichloromethane (185 mL, 10 volumes) then water (185 mL, 10 volumes) were added and the layers were separated. The organic layer was dried over magnesium sulfate and filtered. The dichloromethane was removed under vacuum to leave an orange paste. The orange paste was diluted with 10 volumes of 1:1 EtOAc:Hexanes (v/v) and slurried at 25° C. for 16 hours. The mixture was filtered and the filter cake washed with 55-60 mL of 1:1 EtOAc:Hexanes (v/v) and dried to give 24.22 g of 3-(4-Bromo-2,6-difluoro-benzyloxy)-5-methanesulfonyl-isothiazole-4-carboxylic acid methyl ester (70% yield). $^1$H NMR: (DMSO-d6) δ 7.57 (m, 2H); 5.46 (s, 2H); 3.80 (s, 3H); 3.57 (s, 3H). MS (API-ES pos): 442/444 (M+H)$^+$; 205/207 (1,5-difluoro-3-bromotropylium ion), base.

Example 8

Preparation of 5-Amino-3-(4-bromo-2,6-difluoro-benzyloxy)-isothiazole-4-carboxylic acid methyl ester

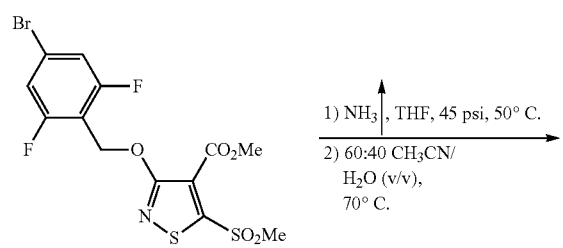

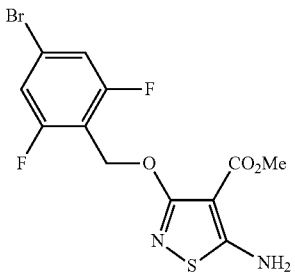

In a 1 L autoclave 3-(4-Bromo-2,6-difluoro-benzyloxy)-5-methanesulfonyl-isothiazole-4-carboxylic acid methyl ester (1.00 equiv, 28.0 g) was taken up in tetrahydrofuran (840 mL, 30 volumes). The vessel was evacuated, heated to 50° C., then placed under 45 psi of anhydrous ammonia gas. The mixture was stirred at 600 rpm for 3 days, then 1000 rpm for an additional 21 hours. The mixture was cooled to 25° C., purged with nitrogen, then the tetrahydrofuran was removed on a rotovap. A 60:40 acetonitrile/water (v/v) solution (240 ml, 10 volumes with respect to theoretical product mass) was added to the residue. The slurry was heated to 70° C. for 1 hour then stirred at 25° C. overnight. The slurry was filtered and the filter cake rinsed with 60:40 acetonitrile/water (v/v) (40 mL). The solids were dried under vacuum to give 21.55 g of 5-Amino-3-(4-bromo-2,6-difluoro-benzyloxy)-isothiazole-4-carboxylic acid methyl ester (90% yield). $^1$H NMR (DMSO-d$_6$) δ 7.87 (s, 2H); 7.52 (m, 2H); 5.26 (s, 2H); 3.60 (s, 3H). MS: (API-ES pos) 379/381 (M+H)$^+$; 205/207 (1,5-difluoro-3-bromotropylium ion), base.

Example 9

Preparation of Imidazole-1-carboxylic acid (4-pyrrolidin-1-yl-butyl)-amide

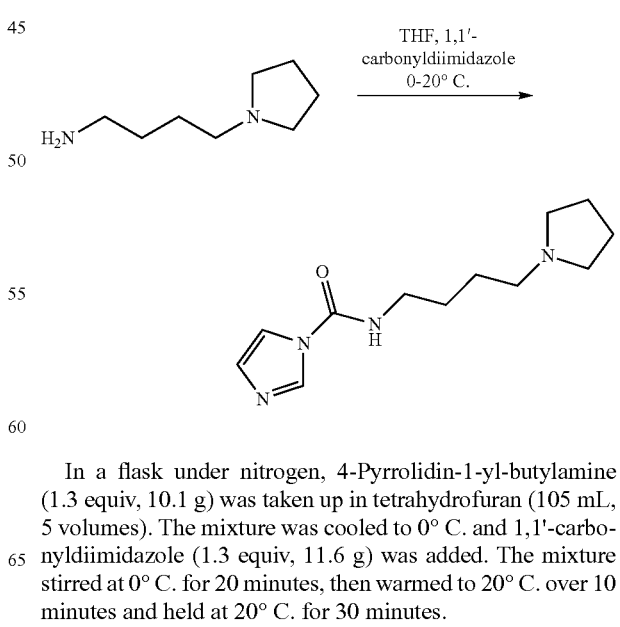

In a flask under nitrogen, 4-Pyrrolidin-1-yl-butylamine (1.3 equiv, 10.1 g) was taken up in tetrahydrofuran (105 mL, 5 volumes). The mixture was cooled to 0° C. and 1,1'-carbonyldiimidazole (1.3 equiv, 11.6 g) was added. The mixture stirred at 0° C. for 20 minutes, then warmed to 20° C. over 10 minutes and held at 20° C. for 30 minutes.

Example 10

Preparation of 3-(4-Bromo-2,6-difluoro-benzyloxy)-5-[3-(4-pyrrolidin-1-yl-butyl)-ureido]-isothiazole-4-carboxylic acid methyl ester

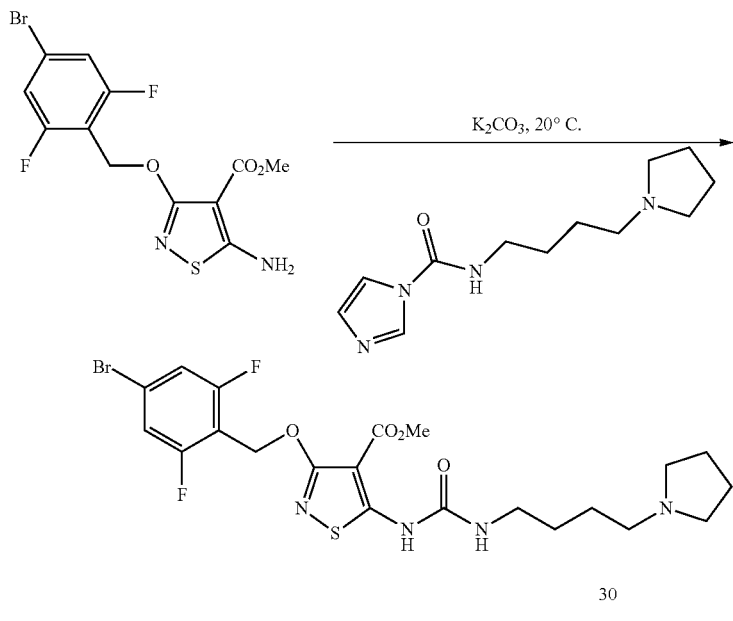

Dimethylsulfoxide (105 mL, 5 volumes) was added to the imidazole-1-carboxylic acid (4-pyrrolidin-1-yl-butyl)-amide/tetrahydrofuran mixture, the tetrahydrofuran was removed by distillation under vacuum. The mixture was cooled to 20° C. then 5-Amino-3-(4-bromo-2,6-difluoro-benzyloxy)-isothiazole-4-carboxylic acid methyl ester (1.00 equiv, 21.0 g) was added, followed by potassium carbonate (2.0 equiv, 15.2 g). The mixture stirred at 20° C. for 21.5 hours. Ethyl acetate (210 mL, 10 volumes) then water (210 mL, 10 volumes) were added. The slurry was stirred at 20° C. for 3-4 hours. The solids were filtered and the filter cake was rinsed with ethyl acetate (63.0 mL, 3 volumes). The solids were dried in a vacuum oven for 17 hours to give 27.36 grams of 3-(4-Bromo-2,6-difluoro-benzyloxy)-5-[3-(4-pyrrolidin-1-yl-butyl)-ureido]-isothiazole-4-carboxylic acid methyl ester (90% yield). $^1$H NMR: (DMSO-d6) δ 10.38 (s, 1H); 8.11 (m, 1H); 7.54 (m, 2H); 5.30 (s, 2H); 3.70 (s, 3H); 3.12 (m, 2H); 2.48 (m, 6H); 1.63 (m, 4H); 1.44 (m, 4H). MS (API-ES pos): 547/549 (M+H)$^+$, base.

Example 11

Preparation of 3-(4-Bromo-2,6-difluoro-benzyloxy)-5-[3-(4-pyrrolidin-1-yl-butyl)-ureido]-isothiazole-4-carboxylic acid amide

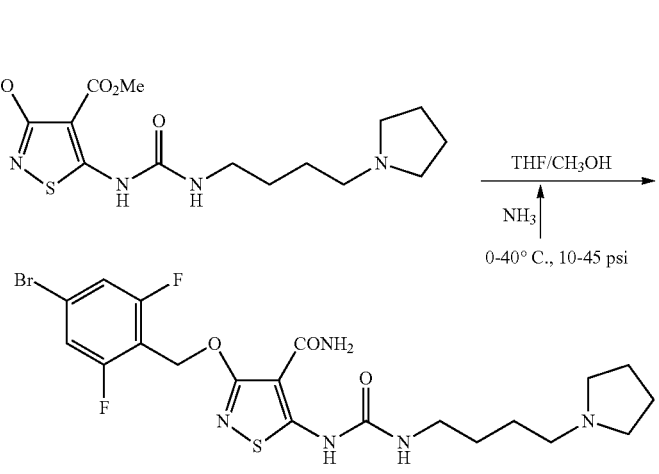

In a 1 Liter autoclave 3-(4-Bromo-2,6-difluoro-benzyloxy)-5-[3-(4-pyrrolidin-1-yl-butyl)-ureido]-isothiazole-4-carboxylic acid methyl ester (1.00 equiv, 27.0 g) was slurried in methanol (270 mL, 10 volumes) and tetrahydrofuran (270 mL, 10 volumes). The mixture was cooled to 0° C. and stirred at 600 rpm. Anhydrous ammonia gas was charged carefully, keeping the temperature below 10° C. Once a steady pressure of around 10 psi was maintained, the mixture was heated to 40° C. The pressure increased to about 45 psi. The pressure was adjusted to 50 psi and stirred at 600 rpm and 40° C. for 90 hours. The stir rate was then adjusted to 1000 rpm and stirred for an additional 24 hours. The ammonia was removed by vacuum, and the mixture was cooled to 20° C. and transferred out of the reactor. The mixture was filtered to remove insoluble solids (non-product related). The filtrate was diluted with 2-propanol (270 mL, 10 volumes), and the tetrahydrofuran and methanol were distilled atmospherically. Additional 2-propanol (135 mL, 5 volumes) were added, then the mixture was distilled to approximately 250 mL total volume. The slurry was cooled to 20° C. and stirred 18 hours. The solids were filtered and then dried under vacuum to give 19.9 grams of 3-(4-Bromo-2,6-difluoro-benzyloxy)-5-[3-(4-pyrrolidin-1-yl-butyl)-ureido]-isothiazole-4-carboxylic acid amide (76% yield). $^1$H NMR (DMSO-d$_6$): δ 10.98 (s, 1H); 8.18 (m, 1H); 7.55 (m, 3H); 6.80 (s, 1H); 5.41 (s, 2H); 3.08 (m, 2H); 2.47 (m, 6H); 1.62 (m, 4H); 1.42 (m, 4H). MS (API-ES pos) 532/534 (M+H)$^+$, base.

What is claimed is:

1. A process for the preparation of a compound of Formula II

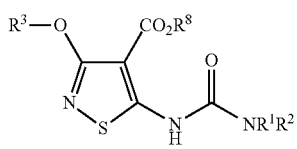

II or a pharmaceutically acceptable salt thereof, wherein
$R^1$ is H, $C_1$-$C_{10}$ alkyl, $C_2$-$C_{10}$ alkenyl, $C_2$-$C_{10}$ alkynyl, —C(O)($C_1$-$C_{10}$ alkyl), —(CH$_2$)$_t$($C_6$-$C_{10}$ aryl), —(CH$_2$)$_t$(4-10 membered heterocyclic), —C(O)(CH$_2$)$_t$($C_6$-$C_{10}$ aryl), or —C(O)(CH$_2$)$_t$(4-10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic $R^1$ groups are optionally fused to a $C_6$-$C_{10}$ aryl group, a $C_5$-$C_8$ saturated cyclic group, or a 4-10 membered heterocyclic group;

1 or 2 carbon atoms in the foregoing heterocyclic moieties are optionally substituted by an oxo (=O) moiety; and the foregoing $R^1$ groups, except H, are optionally substituted by 1 to 3 $R^4$ groups;

$R^2$ is selected from the list of substituents provided in the definition of $R^1$, —SO$_2$(CH$_2$)$_t$($C_6$-$C_{10}$ aryl), —SO$_2$(CH$_2$)$_t$(4-10 membered heterocyclic), and —OR$^5$, t is an integer ranging from 0 to 5, and the foregoing $R^2$ groups are optionally substituted by 1 to 3 $R^4$ groups;

or $R^1$ and $R^2$ may be taken together with the nitrogen to which each is attached to form a 4-10 membered saturated monocyclic or polycyclic ring or a 5-10 membered heteroaryl ring, wherein said saturated and heteroaryl rings optionally include 1 or 2 heteroatoms selected from O, S and —N(R$^6$)— in addition to the nitrogen to which $R^1$ and $R^2$ are attached, said —N(R$^6$)— is optionally =N— or —N= where $R^1$ and $R^2$ are taken together as said heteroaryl group, said saturated ring optionally may be partially unsaturated by including 1 or 2 carbon-carbon double bonds, and said saturated and heteroaryl rings, including the R$^6$ group of said —N(R$^6$)—, are optionally substituted by 1 to 3 R$^4$ groups;

$R^3$ is H, $C_1$-$C_{10}$ alkyl, $C_2$-$C_{10}$ alkenyl, $C_2$-$C_{10}$ alkynyl, —(CH$_2$)$_t$($C_6$-$C_{10}$ aryl), or —(CH$_2$)$_t$(4-10 membered heterocyclic), wherein t is an integer from 0 to 5; said alkyl group optionally includes 1 or 2 hetero moieties selected from O, S and —N(R$^6$)— with the proviso that two O atoms, two S atoms, or an O and S atom are not attached directly to each other; said aryl and heterocyclic $R^3$ groups are optionally fused to a $C_6$-$C_{10}$ aryl group, a $C_5$-$C_8$ saturated cyclic group, or a 4-10 membered heterocyclic group;

1 or 2 carbon atoms in the foregoing heterocyclic moieties are optionally substituted by an oxo (=O) moiety; the —(CH$_2$)$_t$— moieties of the foregoing $R^3$ groups optionally include a carbon-carbon double or triple bond where t is an integer from 2 to 5, and the foregoing $R^3$ groups are optionally substituted by 1 to 5 $R^4$ groups;

each $R^4$ is independently selected from halo, $C_1$-$C_{10}$ alkyl, $C_2$-$C_{10}$ alkenyl, $C_2$-$C_{10}$ alkynyl, nitro, trifluoromethyl, trifluoromethoxy, azido, —OR$^5$, —NR$^6$C(O)OR$^5$, —NR$^6$SO$_2$R$^5$, —SO$_2$NR$^5$R$^6$, —NR$^6$C(O)R$^5$, —C(O)NR$^5$R$^6$, —NR$^5$R$^6$, —S(O)$_j$R$^7$ wherein j is an integer ranging from 0 to 2, —NR$^5$(CR$^6$R$^7$)$_t$OR$^6$, —(CH$_2$)$_t$($C_6$-$C_{10}$ aryl), —SO$_2$(CH$_2$)$_t$($C_6$-$C_{10}$ aryl), —S(CH$_2$)$_t$($C_6$-$C_{10}$ aryl), —O(CH$_2$)$_t$($C_6$-$C_{10}$ aryl), —(CH$_2$)$_t$(4-10 membered heterocyclic), and —(CR$^6$R$^7$)$_m$OR$^6$, wherein m is an integer from 1 to 5 and t is an integer from 0 to 5; said alkyl group optionally contains 1 or 2 hetero moieties selected from O, S and —N(R$^6$)— with the proviso that two O atoms, two S atoms, or an O and S atom are not attached directly to each other; said aryl and heterocyclic R$^4$ groups are optionally fused to a $C_6$-$C_{10}$ aryl group, a $C_5$-$C_8$ saturated cyclic group, or a 4-10 membered heterocyclic group; 1 or 2 carbon atoms in the foregoing heterocyclic moieties are optionally substituted by an oxo (=O) moiety; and the alkyl, aryl and heterocyclic moieties of the foregoing R$^4$ groups are optionally substituted by 1 to 3 substituents independently selected from nitro, trifluoromethyl, trifluoromethoxy, azido, —NR$^6$SO$_2$R$^5$, —SO$_2$NR$^5$R$^6$, —NR$^6$C(O)R$^5$, —C(O)NR$^5$R$^6$, —NR$^5$R$^6$, —(CR$^6$R$^7$)$_m$OR$^6$ wherein m is an integer from 1 to 5, —OR$^5$ and the substituents listed in the definition of R$^5$;

each R$^5$ is independently selected from H, $C_1$-$C_{10}$ alkyl, —(CH$_2$)$_t$($C_6$-$C_{10}$ aryl), and —(CH$_2$)$_t$(4-10 membered heterocyclic), wherein t is an integer from 0 to 5;

said alkyl group optionally includes 1 or 2 hetero moieties selected from O, S and —N(R$^6$)— with the proviso that two O atoms, two S atoms, or an O and S atom are not attached directly to each other; said aryl and heterocyclic R$^5$ groups are optionally fused to a $C_6$-$C_{10}$ aryl group, a $C_5$-$C_8$ saturated cyclic group, or a 4-10 membered heterocyclic group; and the foregoing R$^5$ substituents, except H, are optionally substituted by 1 to 3 substituents independently selected from nitro, trifluoromethyl, trifluoromethoxy, azido, —NR$^6$C(O)R$^7$, —C(O)NR$^6$R$^7$, —NR$^6$R$^7$, hydroxy, $C_1$-$C_6$ alkyl, and $C_1$-$C_6$ alkoxy;

each R$^6$ and R$^7$ is independently H or $C_1$-$C_6$ alkyl;
$R^8$ is H, $C_1$-$C_{10}$ alkyl, —C(O)($C_1$-$C_{10}$ alkyl), —C(O)($C_6$-$C_{10}$ aryl), —C(O)(4-10 membered heterocyclic), —(CH$_2$)$_t$($C_6$-$C_{10}$ aryl), —(CH$_2$)$_t$(4-10 membered heterocyclic), —C(O)O($C_1$-$C_{10}$ alkyl); —C(O)O($C_6$-$C_{10}$ aryl), —C(O)O(4-10 membered heterocyclic) wherein t is an integer from 0 to 5;

said aryl and heterocyclic R$^8$ groups are optionally fused to a $C_6$-$C_{10}$ aryl group; and the foregoing aryl and heterocyclic R⁸ groups are optionally substituted with 1-2 substituents independently selected from halogen, trifluoromethyl, $C_1$-$C_6$ alkoxy, $C_1$-$C_6$ alkyl, and nitro groups; comprising (1) reacting a compound of Formula IV

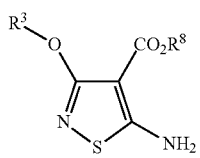

IV wherein $R^3$, $R^4$, $R^5$, $R^6$, $R^7$ and $R^8$ are as defined above for Formula II with a source of carbonyl, with or without an added base, and then adding a compound of Formula III

HNR¹R²  III wherein $R^1$ and $R^2$ are as defined above for Formula II in a solvent to give a compound of the Formula II or (2) reacting a compound of Formula III with a source of carbonyl, with or without an added base, and then adding a compound of Formula IV in a solvent to give a compound of the Formula II, wherein the compound of Formula II is selected from the group consisting of:

3-(4-Bromo-2,6-difluoro-benzyloxy)-5-[3-(4-pyrrolidin-1-yl-butyl)-ureido}-isothiazole-4-carboxylic acid methyl ester;

5-{3-[3-(4-Methyl-piperazin-1-yl)-propyl]-ureido}-3-(2,3,6-trifluoro-4-methyl-benzyloxy-isothiazole-4-carboxylic acid methyl ester;

3-(4-Chloro-2,6-difluoro-benzyloxy)-5-(3-{4-[ethyl-(2-hydroxy-ethyl)-amino]-butyl}-ureido)-isothiazole-4-carboxylic acid methyl ester;

3-(2-Fluoro-4-methyl-benzyloxy)-5-{3-[3-(4-methyl-piperazin-1-yl)-propyl]-ureido}-isothiazole-4-carboxylic acid methyl ester;

3-(2,5-Difluoro-4-methyl-benzyloxy)-5-(3-4-[4-(2-hydroxy-ethyl)-piperazin-1-yl]-butyl}-ureido)-isothiazole-4-carboxylic acid methyl ester;

3-(2,5-Difluoro-4-methyl-benzyloxy)-5-[3-(6-dimethylamino-hexyl)-ureido]-isothiazole-4-carboxylic acid methyl ester;

3-(2-Fluoro-4-methyl-benzyloxy)-5-[3-(5-isopropylamino-pentyl)-ureido]-isothiazole-4-carboxylic acid methyl ester;

hydrochloride salt of 3-(4-Bromo-2,6-difluoro-benzyloxy)-5-[3-(4-pyrrolidin-1-yl-butyl)-ureido}-isothiazole-4-carboxylic acid methyl ester;

3-(4-Chloro-2,6-difluoro-benzyloxy)-5-[3-(4-pyrrolidin-1-yl-butyl)-ureido]-isothiazole-4-carboxylic acid methyl ester;

3-(4-Chloro-2,6-difluoro-benzyloxy)-5-{3-[3-(4-methyl-piperazin-1-yl)-propyl]-ureido}-isothiazole-4-carboxylic acid methyl ester;

3-(4-Chloro-2,6-difluoro-benzyloxy)-5-{3-[-(1-methyl-pyrrolidin-2-yl)-ethyl]-ureido}-isothiazole-4-carboxylic acid methyl ester;

3-(2,6-Difluoro-4-methyl-benzyloxy)-5-[3-(4-pyrrolidin-1-yl-butyl)-ureido]-isothiazole-4-carboxylic acid methyl ester;

3-(2,6-Difluoro-4-methyl-benzyloxy)-5-[3-{4-[4-(2-hydroxy-ethyl)-piperazin-1-yl]-butyl}-ureido)-isothiazole-4-carboxylic acid methyl ester;

3-(4-Chloro-2,6-difluoro-benzyloxy)-5-[3-(3-hydroxy-5-pyrrolidin-1-yl)-pentyl)-ureido}-isothiazole-4-carboxylic acid methyl ester;

3-(2,5-Difluoro-4-methyl-benzyloxy)-5-{3-[4-(3,4-dihydroxy-pyrrolidin-1-yl]-butyl]-ureido}-isothiazole-4-carboxylic acid methyl ester;

3-(4-Chloro-2,6-difluoro-benzyloxy)-5-{3-[4-(3,4-dihydroxy-pyrrolidin-1-yl]-butyl]-ureido}-isothiazole-4-carboxylic acid methyl ester;

3-(2,5-Difluoro-4-methyl-benzyloxy)-5-{3-[4-(2-hydroxymethyl-pyrrolidin-1-yl)-butyl]-ureido}-isothiazole-4-carboxylic acid methyl ester;

3-(4-Chloro-2,6-difluoro-benzyloxy)-5-{3-[4-(2-hydroxymethyl-pyrrolidin-1-yl)-butyl]-ureido}-isothiazole-4-carboxylic acid methyl ester;

3-(2,5-Difluoro-4-methyl-benzyloxy)-5-{3-[4-(3-hydroxy-pyrrolidin-1-yl)-butyl]-ureido}-isothiazole-4-carboxylic acid methyl ester;

3-(4-Bromo-2,6-difluoro-benzyloxy)-5-[3-(4-pyrrolidin-1-yl-butyl]-ureido}-isothiazole-4-carboxylic acid methyl ester;

3-(2,6-Difluoro-4-methyl-benzyloxy)-5-[3-(4-hydroxy-5-piperidin-1-yl-pentyl)-ureido]-isothiazole-4-carboxylic acid methyl ester;

3-(2,5-Difluoro-4-methyl-benzyloxy)-5-{3-[4-(3-hydroxy-5-piperidin-1-yl-pentyl)-ureido]-isothiazole-4-carboxylic acid methyl ester;

3-(4-Chloro-2,6-difluoro-benzyloxy)-5-{3-[4-(2-hydroxymethyl-piperidin-1-yl)-butyl]-ureido}-isothiazole-4-carboxylic acid methyl ester;

3-(2,5-Difluoro-4-methyl-benzyloxy)-5-(3-{4-[ethyl-(2-hydroxy-ethyl)-amino]-butyl}-ureido)-isothiazole-4-carboxylic acid methyl ester;

3-(4-Chloro-2,6-difluoro-benzyloxy)-5-[3-(5-hydroxy-6-piperidin-1-yl)-hexyl)-ureido}-isothiazole-4-carboxylic acid methyl ester;

3-(4-Bromo-2,3,6-trifluoro-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-[3-(3-hydroxy-5-pyrrolidin-1-yl)-pentyl)-ureido]-isothiazole-4-carboxylic acid methyl ester;

5-[3-(4-Pyrrolidin-1-yl-butyl)-ureido]-3-(2,3,6-trifluoro-4-methyl-benzyloxy)-isothiazole-4-carboxylic acid methyl ester;

5-[3-(3-Hydroxy-5-pyrrolidin-1-yl-pentyl)-ureido]-3-(2,3,6-trifluoro-4-methyl-benzyloxy)-isothiazole-4-carboxylic acid methyl ester;

3-(4-Chloro-2,6-difluoro-benzyloxy)-5-{3-[3-(5-methyl-2,5-diazabicyclo[2.2.1]hept-2-yl)-propyl]-ureido}-isothiazole-4-carboxylic acid methyl ester;

3-(4-Chloro-2,3,6-trifluoro-benzyloxy)-5-{3-[3-(5-methyl-2,5-diaza-bicyclo[2.2.1]hept-2-yl)-propyl]-ureido}-isothiazole-4-carboxylic acid methyl ester;

3-(4-Chloro-2,3,6-trifluoro-benzyloxy)-5-{3-[2-(1-methyl-pyrrolidin-2-yl)-ethyl]-ureido}-isothiazole-4-carboxylic acid methyl ester;

3-(4-Chloro-2,3,6-trifluoro-benzyloxy)-5-[3-(4-pyrrolidin-1-yl-butyl)-ureido]-isothiazole-4-carboxylic acid methyl ester;

3-(4-Chloro-2,3,6-trifluoro-benzyloxy)-5-{3-[4-(2-hydroxymethyl-pyrrolidin-1-yl)-butyl]-ureido}-isothiazole-4-carboxylic acid methyl ester;

5-{3-[2-(1-Methyl-pyrrolidin-2-yl)-ethyl]-ureido}-3-(2,3,6-trifluoro-4-methyl-benzyloxy)-isothiazole-4-carboxylic acid methyl ester;

5-[3-(4-Dimethylamino-butyl)-ureido]-3-(2,3,6-trifluoro-4-methyl-benzyloxy)-isothiazole-4-carboxylic acid methyl ester;

5-[3-(3-Dimethylamino-propyl)-ureido]-3-(2,3,6-trifluoro-4-methyl-benzyloxy)-isothiazole-4-carboxylic acid methyl ester;

5-[3-(3-Hydroxy-5-isopropylamino-pentyl)-ureido]-3-(2,3,6-trifluoro-4-methyl-benzyloxy)-isothiazole-4-carboxylic acid methyl ester;

5-[3-(3-Isopropylamino-propyl)-ureido]-3-(2,3,6-trifluoro-4-methyl-benzyloxy)-isothiazole-4-carboxylic acid methyl ester;

5-{3-[4-(4-Methyl-piperazin-1-yl)-butyl]-ureido}-3-(2,3,6-trifluoro-4-methyl-benzyloxy)-isothiazole-4-carboxylic acid methyl ester;

5-(3-{4-[4-(2-Hydroxy-ethyl)-piperazin-1-yl]-butyl}-ureido)-3-(2,3,6-trifluoro-4-methyl-benzyloxy)-isothiazole-4-carboxylic acid methyl ester;

5-[3-(3-Pyrrolidin-1-yl-propyl)-ureido]-3-(2,3,6-trifluoro-4-methyl-benzyloxy)-isothiazole-4-carboxylic acid methyl ester;

5-[3-(4-Hydroxy-5-piperidin-1-yl-pentyl)-ureido]-3-(2,3,6-trifluoro-4-methyl-benzyloxy)-isothiazole-4-carboxylic acid methyl ester;

3-(4Chloro-2,6-difluoro-benzyloxy)-5-[3-(4-imidazol-1-yl-butyl)-ureido]-isothiazole-4-carboxylic acid methyl ester;

5-(3-{4-[Ethyl-(2-hydroxy-ethyl)-amino]-butyl}-ureido)-3-(2,3,6-trifluoro-4-methyl-benzyloxy)-isothiazole-4-carboxylic acid methyl ester;

3-(4-Chloro-(2,3,6-trifluoro-benzyloxy)-5-{3-[4-(2-hydroxymethyl-piperidin-1-yl)-butyl]-ureido}-isothiazole-4-carboxylic acid methyl ester;

3-(4-Chloro-2,3,6-trifluoro-benzyloxy)-5-[3-(3-hydroxy-5-pyrrolidin-1-yl-pentyl)-ureido]-isothiazole-4-carboxylic acid methyl ester;

3-(4-Bromo-2,6-difluoro-benzyloxy)-5-{3-[3-(4-methyl-piperazin-1-yl)-propyl]-ureido}-isothiazole-4-carboxylic acid methyl ester;

3-(2,6-Difluoro-4-methyl-benzyloxy)-5-{3-[2-(1-methyl-pyrrolidin-2-yl)-ethyl]-ureido}-isothiazole-4-carboxylic acid methyl ester;

3-(2,6-Difluoro-4-methyl-benzyloxy)-5-[3-(4-dimethylamino-butyl)-ureido}-isothiazole-4-carboxylic acid methyl ester;

3-(2,6-Difluoro-4-methyl-benzyloxy)-5-[3-(3-dimethylamino-propyl)-ureido]-isothiazole-4-carboxylic acid methyl ester;

3-(4-Bromo-2,3,6-trifluoro-benzyloxy)-5-[3-(4-pyrrolidin-1-yl-butyl)-ureido]-isothiazole-4-carboxylic acid methyl ester;

3-(4-Chloro-2,3,6-trifluoro-benzyloxy)-5-[3-(4-imidazol-1-yl-butyl)-ureido]-isothiazole-4-carboxylic acid methyl ester;

3-(4-Chloro-2,3,6-difluoro-benzyloxy)-5-(3-{3-[ethyl-(2-hydroxy-ethyl)-amino]-propyl}-ureido)-isothiazole-4-carboxylic acid methyl ester;

3-(4-Chloro-2,3,6-trifluoro-benzyloxy)-5-(3-{3-[ethyl-(2-hydroxy-ethyl)-amino]-propyl}-ureido)-isothiazole-4-carboxylic acid methyl ester;

5-[3-(3-Methylamino-propyl)-ureido]-3-(2,3,6-trifluoro-4-methyl-benzyloxy)-isothiazole-4-carboxylic acid methyl ester;

5-[3-(3-Amino-propyl)-3-methyl-ureido]-3-(2,3,6-trifluoro-4-methyl-benzyloxy)-isothiazole-4-carboxylic acid methyl ester;

5-[3-(4-Diethylamino-butyl)-ureido]-3-(2,3,6-trifluoro-4-methyl-benzyloxy)-isothiazole-4-carboxylic acid methyl ester;

3-(2,6-Difluoro-4-methyl-benzyloxy)-5-[3-(3-pyrrolidin-1-yl-propyl)-ureido]-isothiazole-4-carboxylic acid methyl ester;

3-(3-Chloro-2,6-difluoro-4-methyl-benzyloxy)-5-[3-(4-dimethylamino-butyl)-ureido]-isothiazole-4-carboxylic acid methyl ester; and 5-(3-{4-[Bis-(2-hydroxy-ethyl)-amino]-butyl}-ureido)-3-(2,6-difluoro-4-methyl-benzyloxy)-isothiazole-4-carboxylic acid methyl ester;

and pharmaceutically acceptable salts thereof.

2. The process according to claim 1 wherein the compound of Formula II is 3-(4-Bromo-2,6-difluoro-benzyloxy)-5-[3-(4-pyrrolidin-1-yl-butyl)-ureido]-isothiazole-4-carboxylic acid methyl ester.

* * * * *